United States Patent [19]

Mihayashi et al.

[11] Patent Number: 5,194,369
[45] Date of Patent: Mar. 16, 1993

[54] SILVER HALIDE COLOR PHOTOGRAPHIC MATERIAL

[75] Inventors: Keiji Mihayashi; Seiji Ichijima; Toshio Kawagishi; Naoki Saito; Masuji Motoki, all of Kanagawa, Japan

[73] Assignee: Fuji Photo Film Co., Ltd., Kanagawa, Japan

[21] Appl. No.: 668,120

[22] Filed: Mar. 12, 1991

[30] Foreign Application Priority Data

Mar. 12, 1990 [JP] Japan .................................. 2-60735
Jul. 19, 1990 [JP] Japan .................................. 2-191580
Sep. 30, 1990 [JP] Japan .................................. 2-232857

[51] Int. Cl.⁵ .......................... G03C 7/305; G03C 7/36
[52] U.S. Cl. .................................. 430/544; 430/557; 430/957
[58] Field of Search ................. 430/557, 558, 544, 957

[56] References Cited

U.S. PATENT DOCUMENTS

| | | |
|---|---|---|
| 4,095,984 | 6/1978 | Sueyoshi et al. . |
| 4,149,886 | 4/1979 | Tanaka et al. ........................ 430/475 |
| 4,477,563 | 10/1984 | Ichijima et al. ..................... 430/544 |
| 4,579,816 | 4/1986 | Ohlschlager et al. ............... 430/558 |
| 5,006,452 | 4/1991 | Bucci .................................. 430/557 |

FOREIGN PATENT DOCUMENTS

| | | |
|---|---|---|
| 0320939 | 6/1989 | European Pat. Off. ............ 430/558 |
| 1558452 | 2/1969 | France . |
| 2334982 | 7/1977 | France . |
| 1204680 | 9/1970 | United Kingdom . |

Primary Examiner—Lee C. Wright
Attorney, Agent, or Firm—Birch, Stewart, Kolasch & Birch

[57] ABSTRACT

A silver halide color light-sensitive material containing a coupler represented by formula (I):

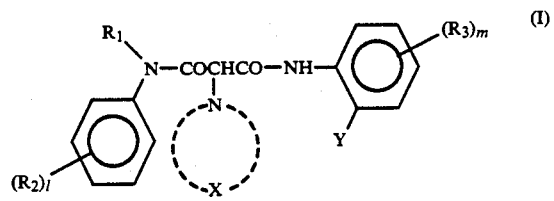

wherein $R_1$ represents a substituted or unsubstituted alkyl group; $R_2$ and $R_3$, same or different, each represent a group capable of substituting a benzene ring; Y represents a halogen atom, an alkoxy group, an alkoxycarbonyl group, a substituted or unsubstituted alkyl group, an alkylthio group, an aryloxy group, an alkylsulfonyl group, an arylthio group, or a carbamoyl group; X represents an organic residue necessary to form a substituted or unsubstituted 5- or 6-membered nitrogen-containing heterocyclic ring together with the nitrogen atom; l represents 0 or an integer of from 1 to 5; and m represents 0 or an integer of from 1 to 4.

The coupler of formula (I) is excellent in dye image stability.

20 Claims, No Drawings

SILVER HALIDE COLOR PHOTOGRAPHIC MATERIAL

FIELD OF THE INVENTION

This invention relates to a silver photographic material having excellent image stability.

BACKGROUND OF THE INVENTION

It is known that couplers in a silver halide color photographic material can react with an oxidation product of an aromatic primary amine color developing agent during color development processing to form an indophenol dye, an indoaniline dye, an azomethine dye, an indaminephenoxazine dye or a like dye, and thereby form a dye image. Color reproduction in such a color formation system is generally achieved by a subtractive color method in which three silver halide emulsions selectively sensitive to blue light, green light, and red light, respectively, are used in combination with complementary yellow, magenta, and cyan couplers, respectively.

Known yellow image-forming couplers include benzoylacetanilide couplers, pivaloylacetanilide couplers, and malondianilide couplers. Examples of the malondianilide yellow couplers are described, e.g., in U.S. Pat. Nos. 4,149,886, 4,095,984, and 4,477,563, and British Patent 1,204,680.

However, these conventional yellow couplers are disadvantageous in that the dye image produced has poor stability particularly to heat and humidity or they have insufficient reactivity with an oxidation product of a developing agent and, therefore, need further improvements. Thus, there has been a demand to develop a yellow coupler having excellent image stability and high reactivity with an oxidation product of a developing

SUMMARY OF THE INVENTION

An object of the present invention is to provide a silver halide color photographic material containing a yellow coupler having excellent image stability and high reactivity with an oxidation product of a developing agent.

The object of the present invention is accomplished by a silver halide color light-sensitive material containing a coupler represented by formula (I):

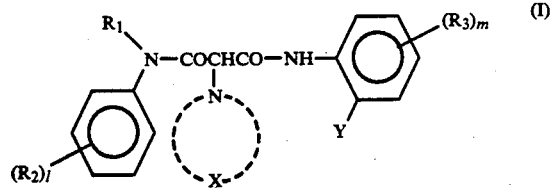

wherein $R_1$ represents an alkyl group; $R_2$ and $R_3$, same or different, each represent a group capable of substituting a benzene ring; Y represents a halogen atom, an alkoxy group, an alkoxycarbonyl group, an alkyl group, an alkylthio group, an aryloxy group, an alkylsulfonyl group, an arylthio group or a carbamoyl group; X represents an organic residue necessary to form a 5- or 6-membered nitrogen-containing heterocyclic ring together with the nitrogen atom; l represents 0 or an integer of from 1 to 5; and m represents 0 or an integer of from 1 to 4.

DETAILED DESCRIPTION OF THE INVENTION

In formula (I), the alkyl group as represented by $R_1$ is a straight chain, branched chain or cyclic, saturated or unsaturated, substituted or unsubstituted alkyl group having from 1 to 20 carbon atoms, preferably from 1 to 10 carbon atoms, and more preferably from 1 to 3 carbon atoms (e.g., methyl, ethyl, propyl, isopropyl, cyclopropyl, octyl, dodecyl). Unsaturated alkyl groups encompassed hereby include alkene and alkyne groups.

Suitabel substituents for the alkyl group $R_1$ include a halogen atom (e.g., fluorine, chlorine), an alkoxy group having from 1 to 20 carbon atoms, and preferably from 1 to 10 carbon atoms (e.g., methoxy, propoxy), a cyano group, a sulfonyl group having from 1 to 20 carbon atoms, and preferably from 1 to 10 carbon atoms (e.g., methanesulfonyl, butanesulfonyl), an alkoxycarbonyl group having from 1 to 20 carbon atoms, and preferably from 1 to 10 carbon atoms (e.g., methoxycarbonyl, butoxycarbonyl), an aryl group having from 6 to 10 carbon atoms (e.g., phenyl), an aryloxy group having from 6 to 10 carbon atoms (e.g., phenoxy), an alkylthio group having from 1 to 20 carbon atoms, and preferably from 1 to 10 carbon atoms (e.g., methylthio, octylthio), and a carboxyl group.

Substituents represented by $R_2$ or $R_3$ include a halogen atom (e.g., fluorine, chlorine), an alkoxycarbonyl group having from 2 to 30 carbon atoms, and preferably from 2 to 20 carbon atoms (e.g., methoxycarbonyl, dodecyloxycarbonyl, hexadecyloxycarbonyl), an acylamino group having from 2 to 30 carbon atoms, and preferably from 2 to 20 carbon atoms (e.g., acetamido, tetradecaneamido, 2-(2,4-di-t-amylphenoxy)-butaneamido, benzamido, a sulfonamido group having from 1 to 30 carbon atoms, and preferably from 1 to 20 carbon atoms (e.g., methanesulfonamido, dodecanesulfonamido, hexadecanesulfonamido, benzenesulfonamido), a carbamoyl group having from 2 to 30 carbon atoms, and preferably from 2 to 20 carbon atoms (e.g., N-butylcarbamoyl, N,N-diethylcarbamoyl), a sulfamoyl group having from 1 to 30 carbon atoms, and preferably from 1 to 20 carbon atoms (e.g., N-butylsulfamoyl, N-dodecylsulfamoyl, N-hexadecylsulfamoyl, N-3-(2,4-di-t-amylphenoxy)butylsulfamoyl), an alkoxy group having from 1 to 30 carbon atoms, and preferably from 1 to 20 carbon atoms (e.g., methoxy, dodecyloxy), a substituted or unsubstituted alkyl group (having the same meaning as described with respect to $R_1$), an N-acylsulfamoyl group having from 2 to 30 carbon atoms, and preferably from 2 to 20 carbon atoms (e.g., N-propanoylsulfamoyl, N-tetradecanoylsulfamoyl), a sulfonyl group having from 1 to 30 carbon atoms, and preferably from 1 to 20 carbon atoms (e.g., methanesulfonyl, octanesulfonyl, dodecanesulfonyl), an alkoxycarbonylamino group having from 1 to 30 carbon atoms, and preferably from 1 to 20 carbon atoms (e.g., methoxycarbonylamino, tetradecyloxycarbonylamino), a cyano group, a nitro group, and a carboxyl group. When l or m represents 2 or more, the plural $R_2$ or $R_3$ groups may be the same or different.

$R_2$ and $R_3$ each preferably represent a halogen atom, an alkyl group, an alkoxycarbonyl group, a sulfamoyl group, a sulfonamido group, or an acylamino group.

Y more specifically represents a halogen atom (e.g., fluorine, chlorine, bromine), an alkoxy group having from 1 to 30 carbon atoms, and preferably from 1 to 20 carbon atoms (e.g., methoxy, ethoxy, tetradecyloxy), an alkoxycarbonyl group having from 1 to 30 carbon atoms, and preferably from 1 to 20 carbon atoms (e.g., methoxycarbonyl, butoxycarbonyl), a substituted or unsubstituted alkyl group (having the same meaning as described with respect to $R_1$), an alkylthio group having from 1 to 30 carbon atoms, and preferably from 1 to 20 carbon atoms (e.g., methylthio, butylthio), an alkylsulfonyl group having from 1 to 30 carbon atoms, and preferably from 1 to 20 carbon atoms (e.g., methanesulfonyl, dodecylsulfonyl), an aryloxy group having from 6 to 10 carbon atoms and preferably having 6 carbon atoms (e.g., phenoxy), an arylthio group having from 6 to 10 carbon atoms and preferably having 6 carbon atoms (e.g., 4-methoxy arylthio) or a carbamoyl group having from 2 to 30 carbon atoms, and preferably from 2 to 20 carbon atoms (e.g., N-dodecylcarbamoyl).

Y preferably represents a halogen atom or an alkoxy group.

The 5- or 6-membered heterocyclic group formed by X and the N atom includes a monocyclic or condensed, substituted or unsubstituted heterocyclic group. Examples of such a heterocyclic group include succinimido, maleinimido, phthalimido, diglycolimido, pyrrolino, pyrazolyl, imidazolyl, 1,2,4-triazol-2-yl (or 4-yl), 1-tetrazolyl, indolyl, benzopyrazolyl, benzimidazolyl, benzotriazolyl , imidazolidine-2,4-dion-3-yl (or 1-yl), oxazolidine-2,4-dion-3-yl, thiazolidine-2,4-dion-3-yl, imidazolin-2-on-1-yl, oxazolin-2-on-3-yl, thiazolin-2-on-3-yl, benzoxazolin-2-on-3-yl, 1,2,4-triazolidine-3,5-dion-4-yl, 2-pyridon-1-yl, morpholine-3,5-dion-4-yl, 1,2,3-triazol-1-yl, and 2-imidazolin-5-one groups.

Suitable substituents for these heterocyclic groups include a halogen atom (e.g., fluorine, chlorine, bromine, iodine), a hydroxyl group, a nitro group, a cyano group, a carboxyl group or a salt thereof, a sulfo group or a salt thereof, a sulfonate group, a sulfinate group, an alkyl group (e.g., methyl, ethyl, n-decyl, t-butyl, trifluoromethyl, carboxymethyl), an alkoxy group (e.g., methoxy, ethoxy, methoxyethoxy), an acyl group (e.g., acetyl, benzoyl), an alkoxycarbonyl group (e.g., methoxycarbonyl, isoamyloxycarbonylmethoxycarbonyl, ethoxycarbonyl, i-propoxycarbonyl, n-dodecyloxycarbonyl), a carbamoyl group (e.g., N,N-dimethylcarbamoyl, N-phenylcarbamoyl, N-methoxyethylcarbamoyl, N-tetradecylcarbamoyl), a sulfonyl group (e.g., methanesulfonyl, benzenesulfonyl, 4-hydroxybenzenesulfonyl), a sulfamoyl group (e.g., N-methylsulfamoyl, N-phenylsulfamoyl, N-dodecylsulfamoyl), a carbonamido group (e.g., acetamido, benzamido, trifluoroacetamido, pentafluorobenzamido), a sulfonamido group (e.g., methanesulfonamido, p-toluenesulfonamido), an amino group (e.g., amino, N,N-dimethylamino, N,N-diethylamino, pyrrolidino, piperidino), an aryloxycarbonyl group (e.g., phenoxycarbonyl), and an alkylthio group (e.g., hexylthio, octylthio).

The 5- or 6-membered heterocyclic group formed by X and N have a total carbon atom number of from 2 to 30, and preferably from 3 to 20, inclusive of the carbon atoms in the substituents, if any.

Preferred heterocyclic groups formed by X and N include 1-pyrazolyl, imidazolyl, 1,2,3-triazol-1-yl, benzotriazolyl, 1,2,4-triazol-1-yl, oxazolidine-2,4-dion-3-yl, 1,2,4-triazolidine-3,5-dion-4-yl, and imidazolidine-2,4-dion-3-yl groups, each of which may have one or more of the above-described substituents.

The couplers represented by formula (I) are used as general two-equivalent yellow couplers or development inhibitor-releasing (DIR) couplers. Where they are used as DIR couplers, the nitrogen-containing heterocyclic group bonded to the coupling position preferably includes a benzotriazolyl group, a 1,2,4-triazolyl group, and a 1,2,3-triazolyl group. Specific examples of such a development inhibitor are described in U.S. Pat. Nos. 4,477,563 and 3,933,500 and West German Patent (OLS) No. 3,644,416.

Of the couplers represented by formula (I), particularly useful as DIR couplers are those represented by formula (II):

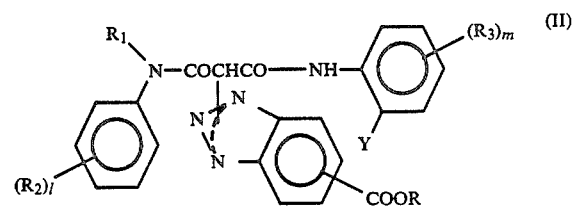

wherein $R_1$, $R_2$, $R_3$, Y, l, and m are as defined above; and R represents a substituted or unsubstituted alkyl group having from 1 to 4 carbon atoms (exclusive of its substituents).

The detailed explanation and specific examples described for $R_1$, $R_2$, $R_3$, Y, l, and m with reference to formula (I) are applied to formula (II).

The alkyl group as represented by R is a straight chain or branched chain, substituted or unsubstituted alkyl group having from 1 to 4 carbon atoms, and preferably from 1 to 3 carbon atoms, exclusive of carbon atoms in its substituent(s), if any.

R is preferably a substituted alkyl group. Suitable substituents include an alkoxycarbonyl group having from 2 to 6 carbon atoms (e.g., methoxycarbonyl, propoxycarbonyl, butoxycarbonyl, isobutoxycarbonyl, isopropoxycarbonyl, pentyloxycarbonyl, isopentyloxycarbon yl, 2-methoxyethoxycarbonyl), a carbamoyl group having from 1 to 9 carbon atoms (e.g., N,N-diethylcarbamoyl, N-methyl-N-ethylcarbamoyl, N-hexylcarbamoyl, pyrrolidinocarbonyl, piperidinocarbonyl), a halogen atom (e.g., chlorine, fluorine), a nitro group, a cyano group, an alkoxy group having from 1 to 4 carbon atoms (e.g., methoxy, ethoxy, methoxyethoxy), a sulfamoyl group having up to 6 carbon atoms (e.g., N,N-diethylsulfamoyl, N-methyl-N-ethylsulfamoyl), an aryloxy group having from 6 to 10 carbon atoms (e.g., 4-chlorophenoxy), an acyl group having from 2 to 7 carbon atoms (e.g., acetyl, benzoyl), a sulfonyl group having from 1 to 6 carbon atoms (e.g., methanesulfonyl, butanesulfonyl), a 3- to 6-membered heterocyclic group having from 1 to 5 carbon atoms and a hetero atom selected from nitrogen, oxygen and sulfur atoms (e.g., 2-pyridyl, 3-pyridyl), and a phosphoryl group having from 2 to 5 carbon atoms (e.g., O,O-diethylphosphoryl). Preferred of them are an alkoxycarbonyl group and a carbamoyl group.

Specific examples of R include

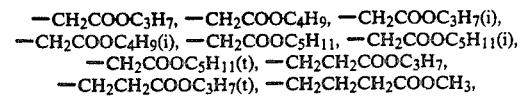

-continued $-CH_2COOCHCH_2CH_3$, $-CH_2CHCOOC_3H_7$,
            $|$                    $|$
            $CH_3$                $CH_3$ $-CH_2CON(C_2H_5)(CH_3)$, $-CH_2CON\text{(pyrrolidinyl)}$, $-CH_2CON\text{(piperidinyl)}$, $-CH_2CH_2CON\text{(pyrrolidinyl)}$, $-CH_2CONHC_4H_9$, $-CH_2CONHC_5H_{11}$, $-CH_2CONHC_4H_9(i)$, $-CH_2CHCl_2$, $-CH_2CF_3$, $-CH_2CF_2CF_3$, $-CH_2CONHC_6H_{13}$, $-CH(CH_2Cl)_2$, $-C_3H_7$, $-C_4H_9$, $-CH_2CH_2OC_2H_5$, $-CH_2SO_2N(CH_2H_5)(C_2H_5)$, $-CH_2CHCO_2CH_3$, and
                                                              $OCH_3$ $-CH_2-\text{(pyridyl)}$ Of the couplers represented by formula (I), particularly useful as general two-equivalent yellow couplers (the releasable group is not a photographically useful group) are those represented by formula (III):

$$R_1\text{N}-\text{COCHCO}-\text{NH}-\text{Ar}(R_3)_m$$
(III)

wherein $R_1$, $R_2$, $R_3$, Y, l, and m are as defined above; and Z represents $$-O-\underset{R_5}{\overset{R_4}{\underset{|}{\overset{|}{C}}}}-,\ -S-\underset{R_5}{\overset{R_4}{\underset{|}{\overset{|}{C}}}}-,\ -\underset{R_6}{\overset{R_4}{\underset{|}{\overset{|}{N}}}}-\underset{R_5}{\overset{|}{C}}-,\ -\underset{R_6}{\overset{|}{N}}-\underset{R_7}{\overset{|}{N}}-,\ -\underset{R_7}{\overset{|}{N}}-\underset{O}{\overset{\|}{C}}-,$$

$$-\underset{R_5}{\overset{R_4}{\underset{|}{\overset{|}{C}}}}-\underset{R_9}{\overset{R_8}{\underset{|}{\overset{|}{C}}}}-,\ \text{or}\ -\underset{R_{10}}{\overset{}{\underset{|}{\overset{}{C}}}}=\underset{R_{11}}{\overset{}{\underset{|}{\overset{}{C}}}}-,$$

wherein $R_4$, $R_5$, $R_8$, and $R_9$, same or different, each represent a hydrogen atom, an alkyl group, an aryl group, an alkoxy group, an aryloxy group, an alkylthio group, an arylthio group, an alkylsulfonyl group, an arylsulfonyl group, or an amino group; $R_6$ and $R_7$, same or different, each represent a hydrogen atom, an alkyl group, an aryl group, an alkylsulfonyl group, an arylsulfonyl group, or an alkoxycarbonyl group; $R_4$ and $R_5$, $R_5$ and $R_6$, $R_6$ and $R_7$, or $R_4$ and $R_8$ each may be taken together to form a ring (e.g., cyclobutane, cyclohexane, cycloheptane, cyclohexene, pyrrolidine, piperidine); and $R_{10}$ and $R_{11}$, same or different, each represent a hydrogen atom, an alkyl group, or an aryl group, or they may be taken together to form a benzene ring.

The alkyl group and alkyl group-containing group represented by $R_4$, $R_5$, $R_6$, $R_7$, $R_8$, $R_9$, $R_{10}$ and $R_{11}$ have preferably from 1 to 30 carbon atoms and more preferably from 1 to 20 carbon atoms in alkyl moiety, and the aryl group and aryl group-containing group represented by $R_4$, $R_5$, $R_6$, $R_7$, $R_8$, $R_9$, $R_{10}$ and $R_{11}$ have preferably from 6 to 20 carbon atoms and more preferably from 6 to 10 carbon atoms.

Of the couplers represented by formula (III), particularly preferred are those wherein Z is $$-O-\underset{R_5}{\overset{R_4}{\underset{|}{\overset{|}{C}}}}-,\ -\underset{R_6}{\overset{R_4}{\underset{|}{\overset{|}{N}}}}-\underset{R_5}{\overset{|}{C}}-\ \text{or}\ -\underset{R_6}{\overset{}{\underset{|}{\overset{}{N}}}}-\underset{R_7}{\overset{}{\underset{|}{\overset{}{N}}}}-.$$

In formula (III), the heterocyclic group bonded at the coupling position has a total carbon atom number of from 2 to 30, and preferably from 4 to 20.

Specific examples of the heterocyclic group bonded at the coupling position are succinimido, maleinimido, phthalimido, 1-methylimidazolidine-2,4-dion-3-yl, 1-benzylimidazolidine-2,4-dion-3-yl, 5,5-dimethyloxazolidine-2,4-dion-3-yl, 5-methyl-5-propyloxazolidine-2,4-dion-3-yl, 5,5-dimethylthiazolidine-2,4-dion-3-yl, 5,5-dimethylimidazolidine-2,4-dion-3-yl, 3-methylimidazolidinetrion-1-yl, 1,2,4-triazolidine-3,5-dion-4-yl, 1-methyl-2-phenyl-1,2,4-triazolidine-3,5-dion-4-yl, 1-benzyl-2-phenyl-1,2,4-triazolidine-3,5-dion-4-yl, 5-hexloxy-1-methylimidazolidine-2,4-dion-3-yl, 1-benzyl-5-ethoxyimidazolidine-2,4-dion-3-yl, and 1-benzyl-5-dodecyloxyimidazolidine-2,4-dion-3-yl groups.

The detailed explanation and specific examples described for $R_1$, $R_2$, $R_3$, Y, l, and m with reference to formula (I) are applied to formula (III).

The couplers represented by formulae (I), (II) or (III) are preferably nondiffusible couplers. The terminology "nondiffusible couplers" as used herein means couplers having in the molecule thereof a group for imparting a sufficiently large molecular weight so that the couplers may be immobilized in a layer where they are added. Usually, an alkyl group having from 8 to 32 carbon atoms, and preferably from 10 to 20 carbon atoms (the term "alkyl group" has the same meaning as previously explained) or an aryl group having a substituent(s) having from 4 to 20 carbon atoms in total (the term "aryl group" has the same meaning as previously explained) is employed as a nondiffusion group for immobilization. The nondiffusible couplers may have one or more of these nondiffusion groups at any position thereof.

The couplers represented by formulae (I), (II) or (III) may be connected at any of $R_1$, $R_2$, $R_3$, Y, X, or Z via a di- or polyvalent linking group to form a polymer inclusive of a dimer. In this case, the carbon atom number in each substituent of these formulae may be out of the above-specified respective range.

Specific examples of the yellow dye-forming couplers of formula (I), (II) or (III) and synthesis examples for some of them are shown below for illustrative purposes only but not for limitation.

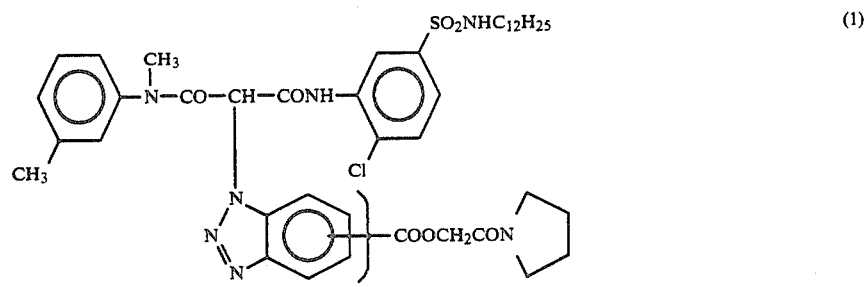
(1)
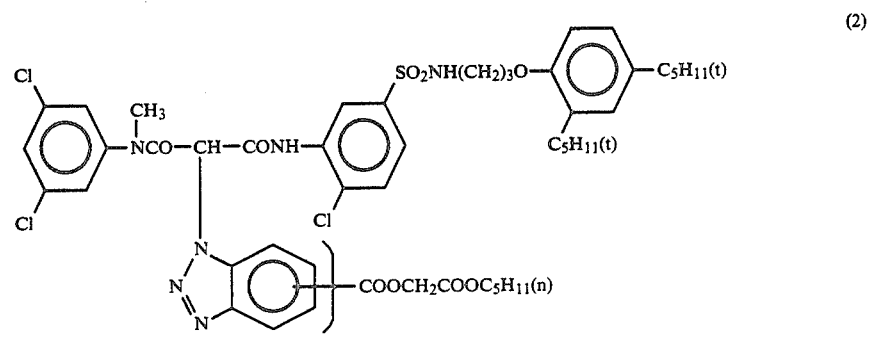
(2)
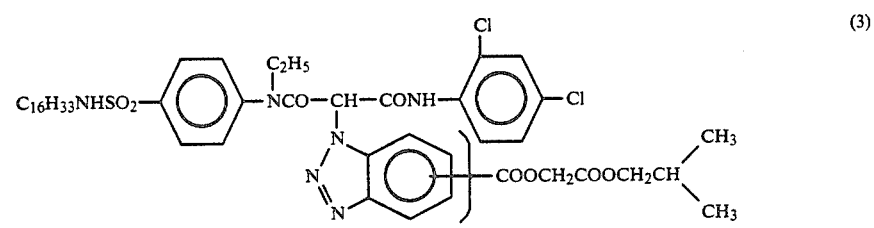
(3)
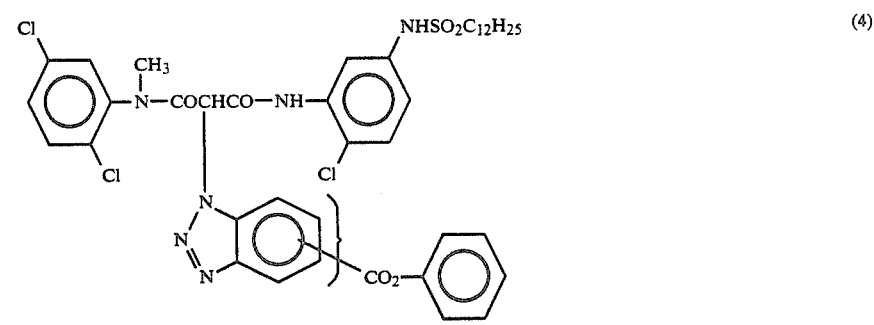
(4)
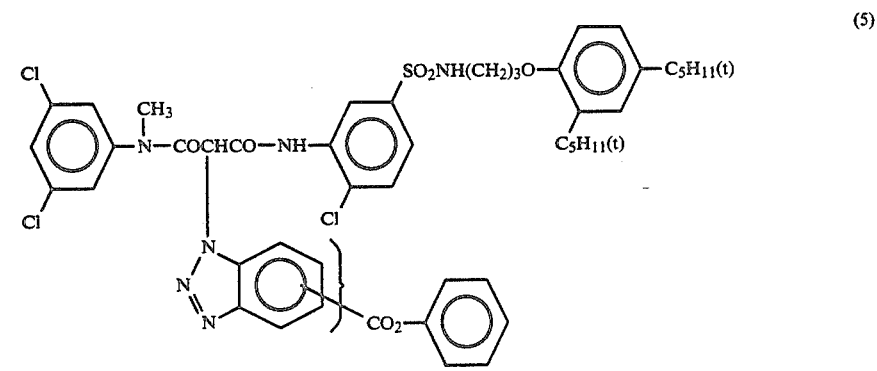
(5)

-continued
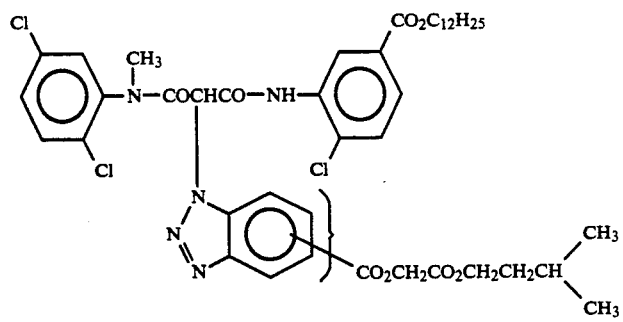 (6)
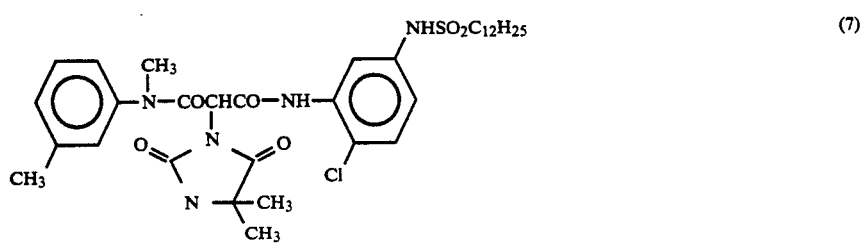 (7)
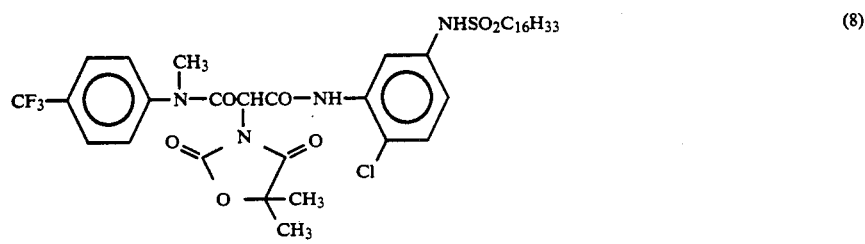 (8)
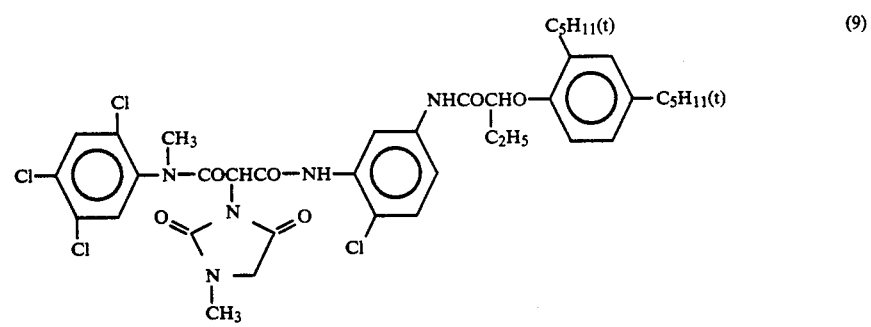 (9)
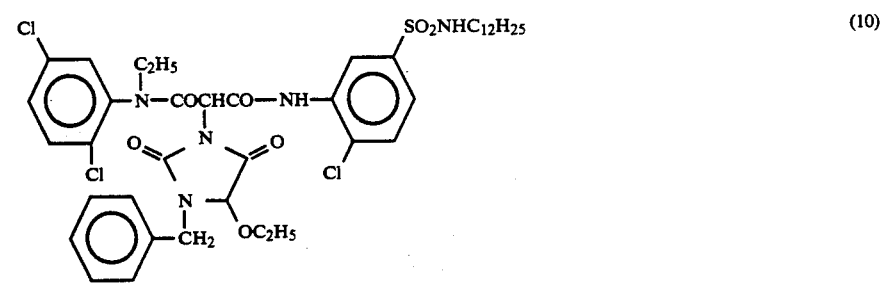 (10)
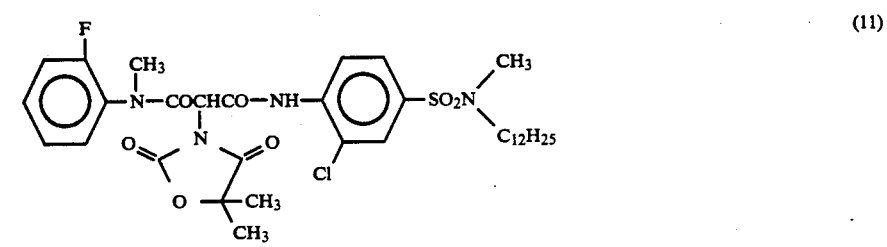 (11)

-continued
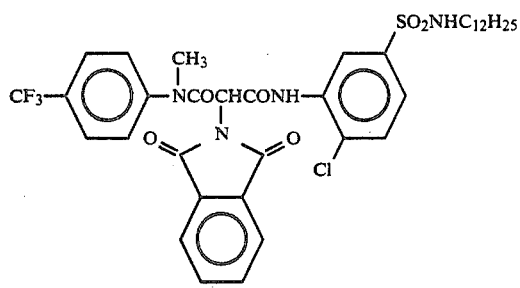
(12)
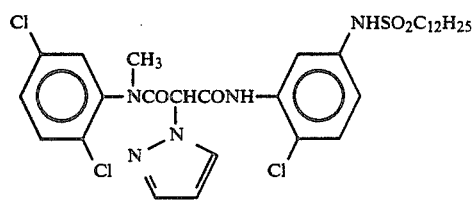
(13)
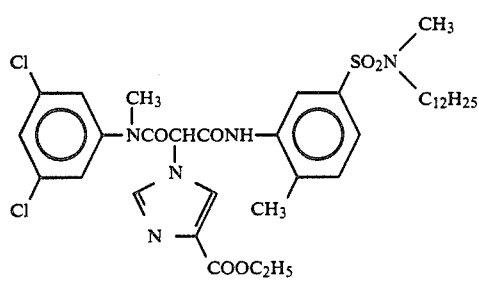
(14)
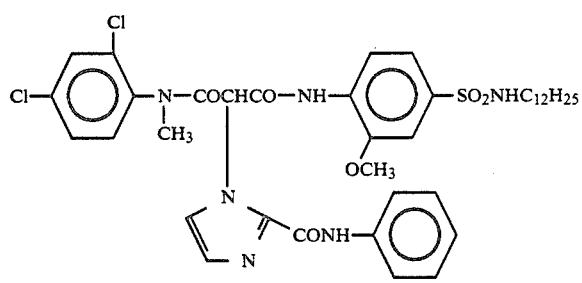
(15)
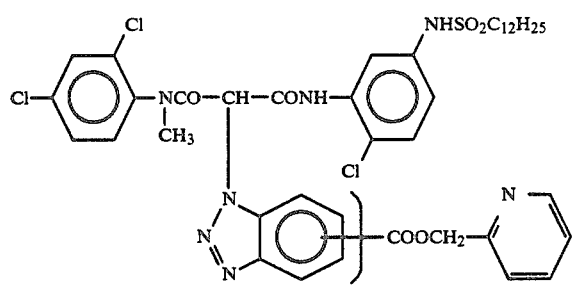
(16)
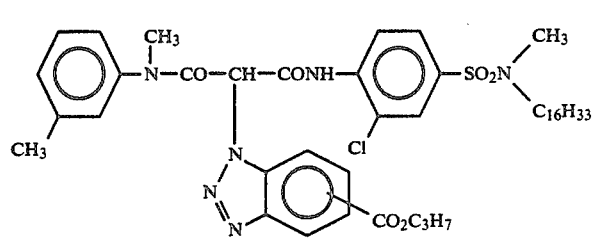
(17)

-continued
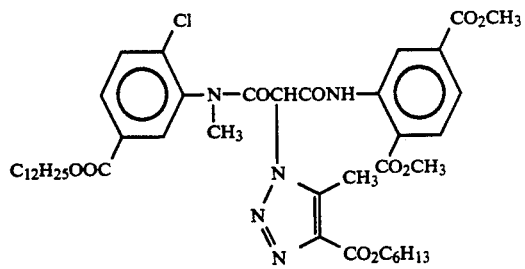 (18)
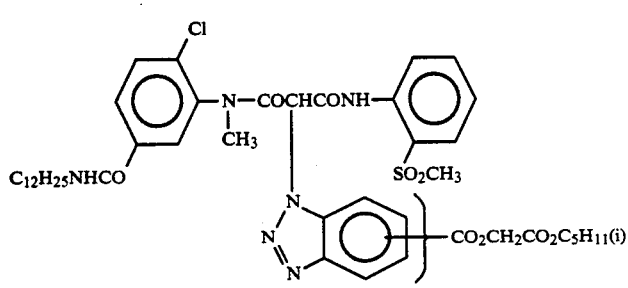 (19)
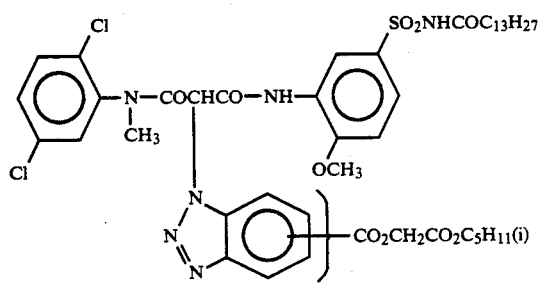 (20)
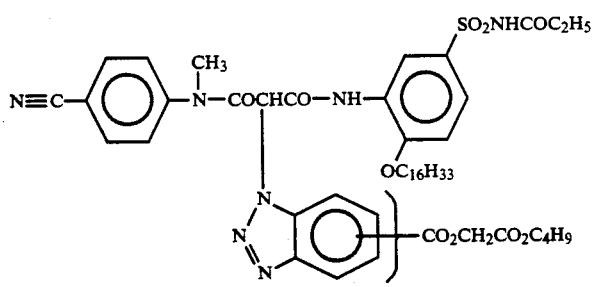 (21)
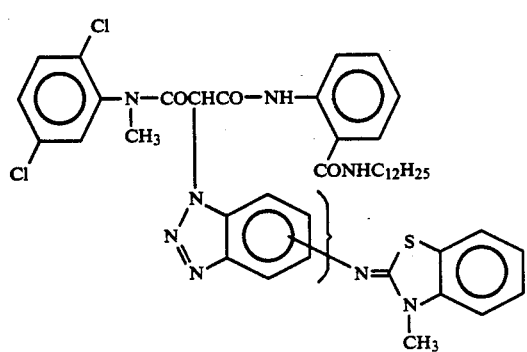 (22)

-continued
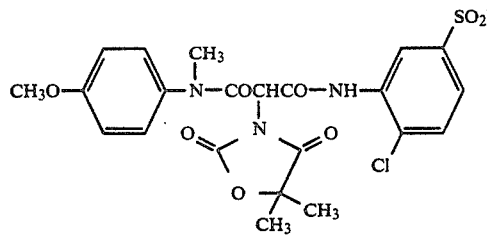
(23)
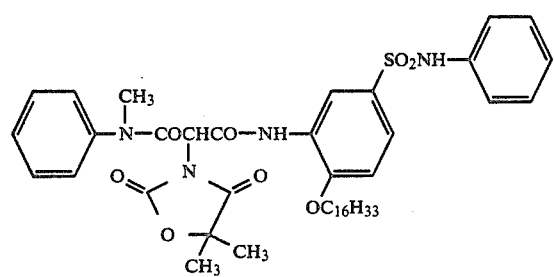
(24)
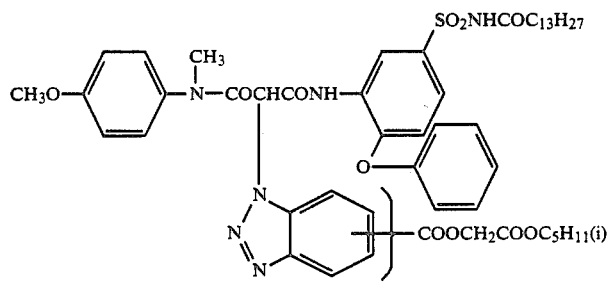
(25)
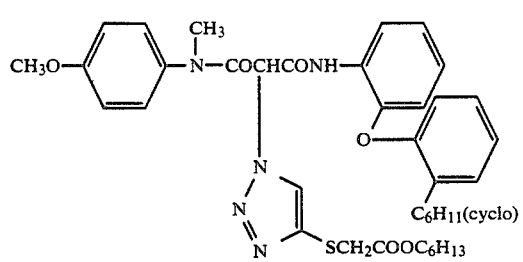
(26)
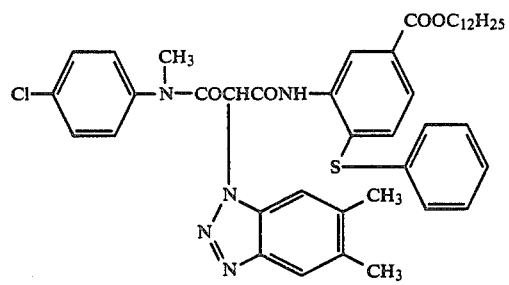
(27)
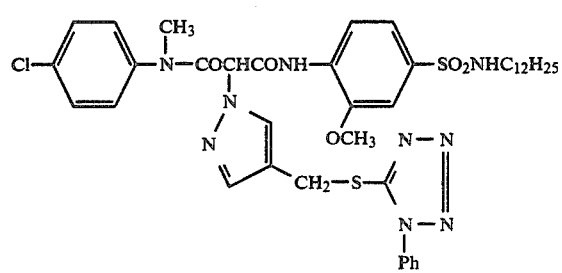
(28)

-continued
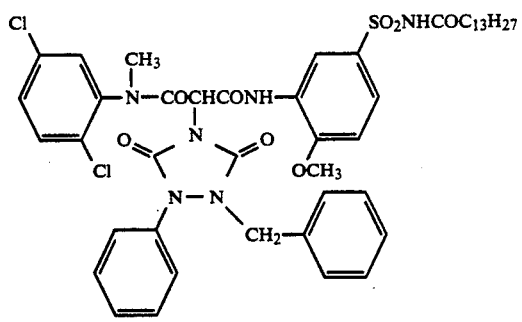 (29)
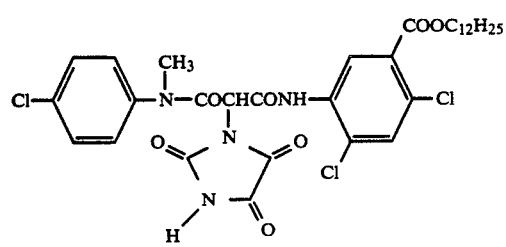 (30)
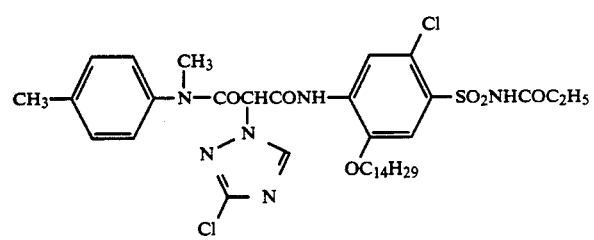 (31)
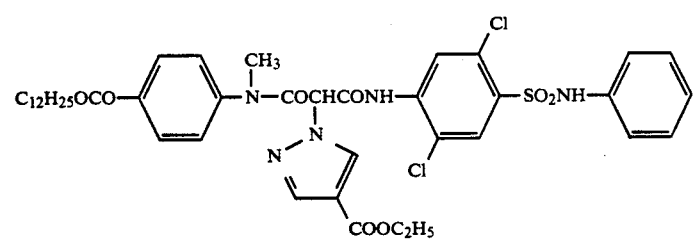 (32)
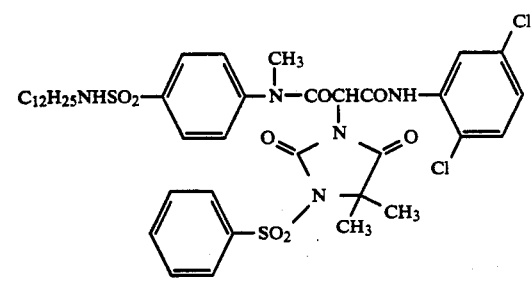 (33)
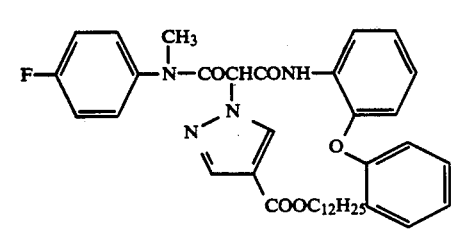 (34)

-continued
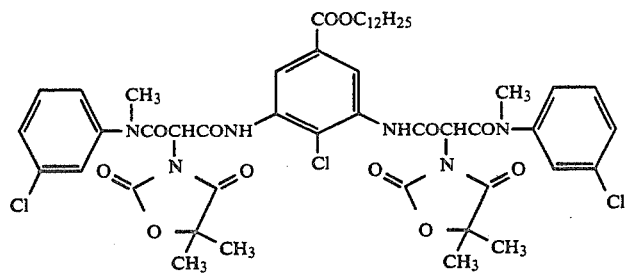
(35)
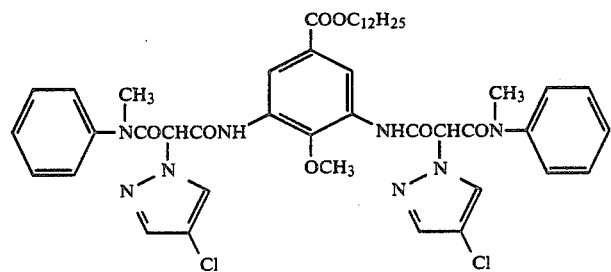
(36)
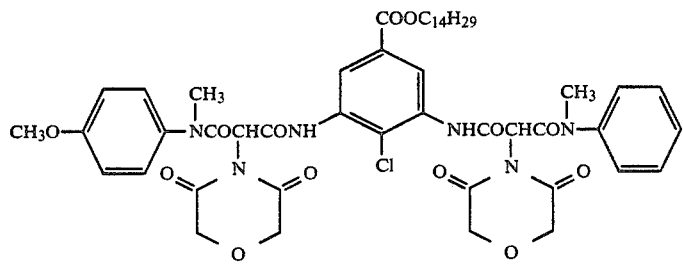
(37)
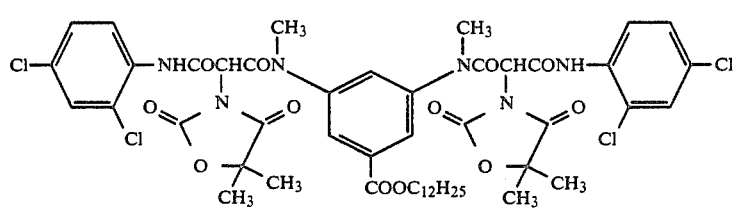
(38)
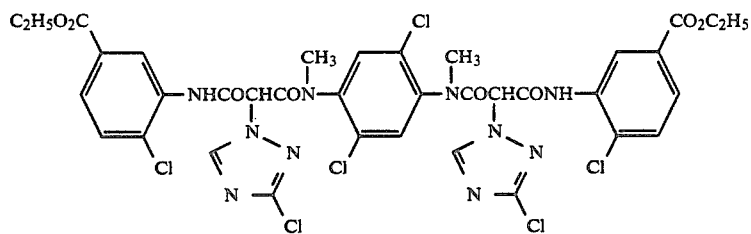
(39)
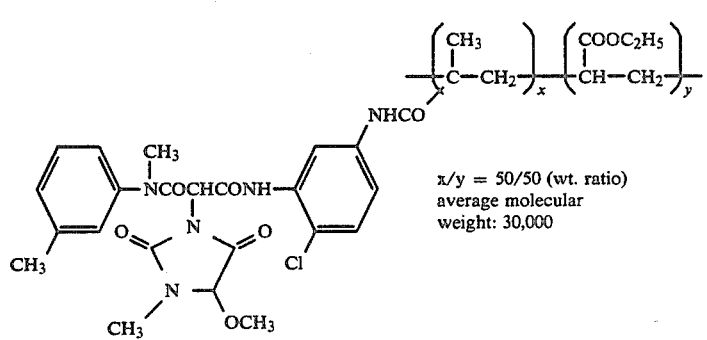
(40)
x/y = 50/50 (wt. ratio)
average molecular weight: 30,000

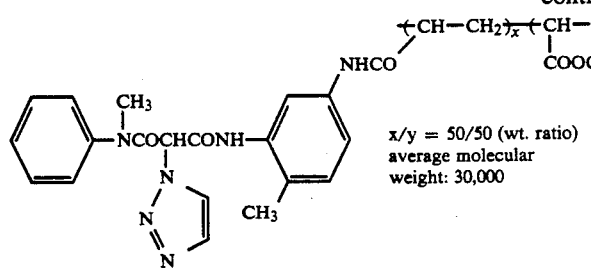
(41)
x/y = 50/50 (wt. ratio)
average molecular weight: 30,000
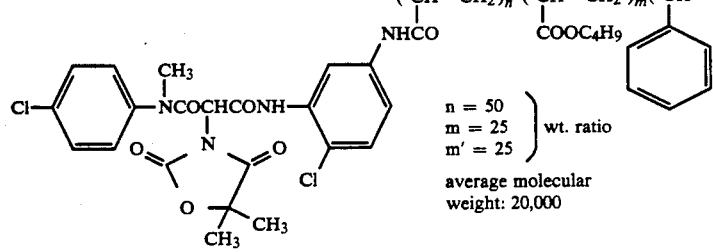
(42)
n = 50
m = 25  } wt. ratio
m' = 25
average molecular weight: 20,000
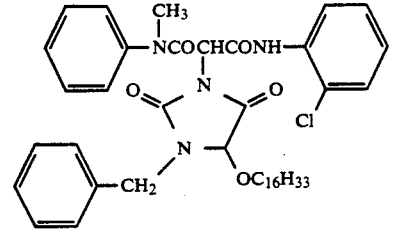
(43)
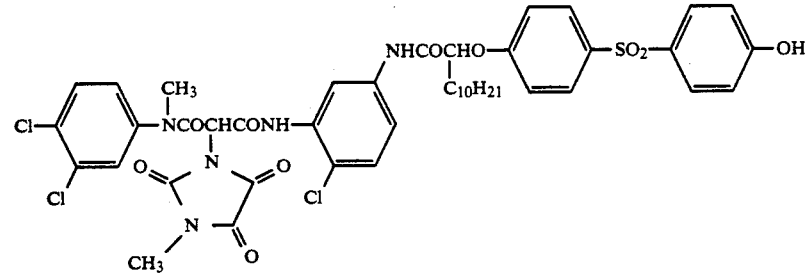
(44)
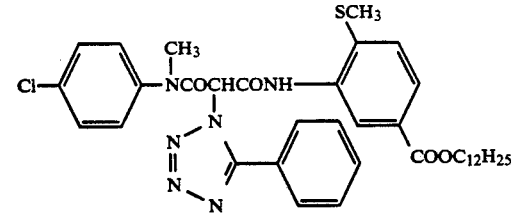
(45)
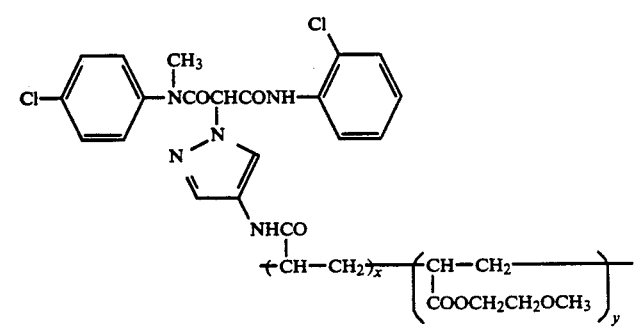
(46)
x/y = 50/50 (wt. ratio)
average molecular weight: 40,000

SYNTHESIS EXAMPLE 1
Synthesis of Compound (1)

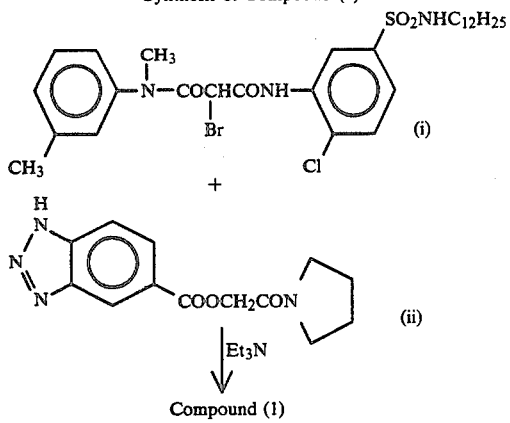

In 200 ml of N,N-dimethylacetamide were dissolved 17.1 g of compound (ii) and 6.3 g of triethylamine, and the solution was stirred for 15 minutes. To the solution was added dropwise a solution of 20 g of compound (i) in 100 ml of chloroform at room temperature over 20 minutes, followed by allowing the mixture to react at room temperature for 3 hours and then at 40° C. for 30 minutes. The reaction mixture was cooled to room temperature, and 200 ml of chloroform was added thereto. The mixture was transferred to a separatory funnel and washed successively with water and diluted hydrochloric acid. Then, the mixture was washed with water until the washing became neutral. The oily layer was separated, and the solvent was removed therefrom by distillation under reduced pressure. The residue was recrystallized from ethyl acetate and hexane to obtain 15.3 g of Compound (1).

SYNTHESIS EXAMPLE 2
Synthesis of Compound (4)

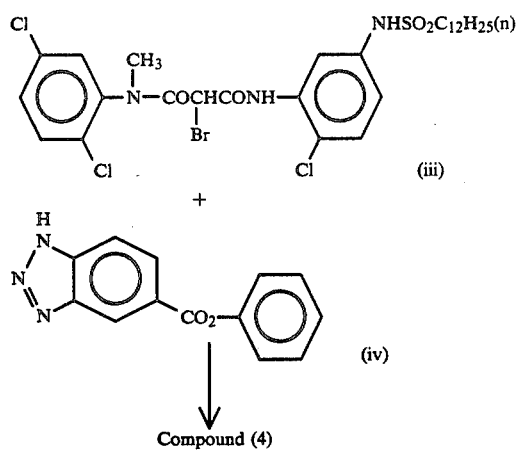

In 50 ml of N,N-dimethylformamide were dissolved 4.42 g of compound (iv) and 1.87 g of triethylamine, followed by stirring for 10 minutes. To the solution was added dropwise a solution of 6.23 g of compound (iii) in 20 ml of methylene chloride at room temperature over 15 minutes. After reacting at room temperature for 1 hour, the reaction mixture was poured into water and extracted with ethyl acetate. The organic layer was dried over magnesium sulfate. The desiccant was removed by filtration, and the solvent was removed by distillation under reduced pressure. The residue was purified by silica gel column chromatography to obtain 4.7 g of Compound (4) as a white powder.

SYNTHESIS EXAMPLE 3
Synthesis of Compound (7)

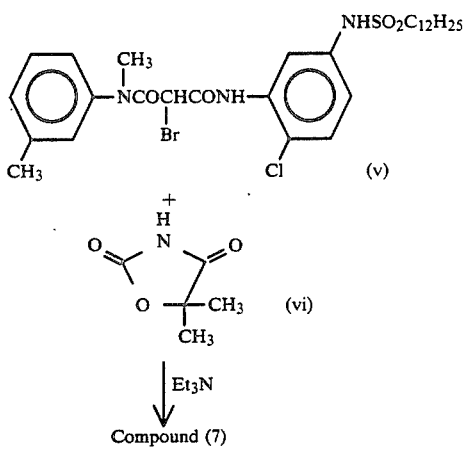

In 200 ml of N,N-dimethylformamide were dissolved 24.3 g of compound (vi) and 26.2 ml of triethylamine, and 200 ml of a chloroform solution containing 50 g of compound (v) was added dropwise to the solution at room temperature, followed by reacting for 3 hours. To the reaction mixture was added 500 ml of water, and the mixture was transferred to a separatory funnel. The oily layer was separated and washed successively with water and diluted hydrochloric acid. The oily layer was then washed with water until the washings became neutral. The oily layer was separated, and the solvent was removed by distillation under reduced pressure. The residue was crystallized from hexane to obtain 23.5 g of Compound (7).

Light-sensitive materials according to the present invention comprise a support having thereon at least one of blue-sensitive, green-sensitive, and red-sensitive silver halide emulsion layers. The number and order of silver halide emulsion layers and light-insensitive layers are not particularly limited. A typical material comprises a support having thereon at least one light-sensitive layer (hereinafter referred to as a unit light-sensitive layer) composed of two or more silver halide emulsion layers which have substantially the same color sensitivity to blue light, green light or red light but which are different in photosensitivity. Multi-layer silver halide color photographic materials generally comprise a support having thereon a red-sensitive unit layer, a green-sensitive unit layer, and a blue-sensitive unit layer in such an order. Depending on the end use, the above order of layers may be altered, or two layers having the same color sensitivity may have therebetween a layer having different color sensitivity.

A light-insensitive layer, including various intermediate layers, may be provided between, above, or below these silver halide light-sensitive layers.

Such intermediate layers may contain couplers, DIR compounds, etc., as described in JP-A-61-43748, JP-A-59-113438, JP-A-59-113440, JP-A-61-20037, and JP-A-61-20038, and may also contain color mixing inhibitors as usual.

Each unit light-sensitive layer preferably has a two-layer structure composed of a high sensitive emulsion layer and a low sensitive emulsion layer as described in West German Patent 1,121,470 and British Patent 923,045. The two layers of each unit light-sensitive layer are generally provided in a descending order of photosensitivity in the direction toward the support. Between the two silver halide emulsion layers, a light-insensitive layer may be provided. It is also possible to provide a low sensitive emulsion layer on the side farther from the support and a high sensitive emulsion layer on the side closer to the support, as described in JP-A-57-112751, JP-A-62-200350, JP-A-62-206541, and JP-A-62-206543.

Specific examples of practical layer orders include an order of low sensitive blue-sensitive layer (BL)/high sensitive blue-sensitive layer (BH)/high sensitive green-sensitive layer (GH)/low sensitive green-sensitive layer (GL)/high sensitive red-sensitive layer (RH)/low sensitive red-sensitive layer (RL)/support, an order of BH/BL/GL/GH/RH/RL/support, and an order of BH/BL/GH/GL/RL/RH/support.

A layer order of blue-sensitive layer/GH/RH/GL/RL/support as described in JP-B-55-34932 (the term "JP-B" as used herein means an examined published Japanese patent application") and a layer order of blue-sensitive layer/GL/RL/GH/RH/support as described in JP-A-56-25738 and JP-A-62-63936 can also be used.

Further, a unit light-sensitive layer may be composed of three layers whose photosensitivity differs in a descending order in the direction toward the support (i.e., the most sensitive silver halide emulsion layer as the upper layer, a middle sensitive silver halide emulsion layer as an intermediate layer, and the least sensitive silver halide emulsion layer as the lower layer) as described in JP-B-49-15495. Three layers of different sensitivity in each unit layer may be arranged in the order of middle sensitive emulsion layer/high sensitive emulsion layer/low sensitive emulsion layer from the side farther from a support, as described in JP-A-59-202464.

Furthermore, an order of high sensitive emulsion layer/low sensitive emulsion layer/middle sensitive emulsion layer or an order of low sensitive emulsion layer/middle sensitive emulsion layer/high sensitive emulsion layer can also be used.

In the case where a unit layer is composed of 4 or more layers, the layer arrangement can be altered similarly.

As mentioned above, a layer structure or arrangement of light-sensitive materials can be appropriately chosen according to the end use.

Silver halide which can be used in the photographic emulsion layers is preferably silver iodobromide, silver iodochloride or silver iodochlorobromide, each having a silver iodide content of at most about 30 mol %, more preferably silver iodobromide or silver iodochlorobromide having a silver iodide content of from about 2 mol % to about 10 mol %.

Silver halide grains of the photographic emulsions may have a regular crystal form, such as a cubic form, an octahedral form, or a tetradecahedral form; an irregular crystal form, such as a spherical form or a plate form; a crystal form having a crystal defect, such as a twinning plane; or a composite crystal form thereof.

Silver halide grains may have a wide variety of grain sizes, ranging from fine grains of about 0.2 μm or smaller to large grains having a projected area diameter reaching about 10 μm. The silver halide emulsion may be either a mono-dispersed emulsion or a poly-dispersed emulsion.

Silver halide photographic emulsions which may be used in the present invention can be prepared by the processes described, e.g., in *Research Disclosure* (hereinafter abbreviated as RD), No. 17643 (Dec., 1978), pp. 22–23, "I. Emulsion Preparation and Types", ibid, No. 18716 (Nov., 1979), p. 648, ibid, No. 307105 (Nov., 1989), pp. 863–865, P. Glafkides, *Chemie et Physique Photographique* (Paul Montel, 1967), G. F. Duffin, *Photographic Emulsion Chemistry* (Focal Press, 1966), and V. L. Zelikman et al., *Making and Coating Photographic Emulsion* (Focal Press, 1964).

Mono-dispersed emulsions described in U.S. Pat. Nos. 3,574,628 and 3,655,394 and British Patent 1,413,748 may be preferably used as well.

Tabular grains having an aspect ratio of about 3 or more are also useful. Such tabular grains can easily be prepared by the processes described, e.g., in Gutoff, *Photographic Science and Engineering*, Vol. 14, pp. 248–257 (1970), U.S. Pat. Nos. 4,434,226, 4,414,310, 4,433,048, and 4,439,520, and British Patent 2,112,157.

The silver halide grains may be homogeneous grains having a uniform crystal structure throughout the individual grains or heterogeneous grains, including those in which the inside and the outer shell have different halogen compositions, those in which the halogen composition differs among layers, and those having fused thereto silver halide of different halogen composition through epitaxy. Silver halide grains fused with compounds other than silver halides, e.g., silver rhodanide or lead oxide, may also be used. A mixture comprising grains of various crystal forms can also be used.

The photographic emulsions may be either the surface latent image type, which forms a latent image predominantly on the surface of grains, or the internal latent image type, which forms a latent image predominantly in the inside of the grains, but they should be of the negative type. Internal latent image type emulsions may be of the core/shell type as described in JP-A-63-264740. The core/shell type internal latent image type emulsions can be prepared by the process described in JP-A-59-133542. The thickness of the shell of this type of emulsion preferably ranges from 3 to 40 nm, particularly from 5 to 20 nm, a though the thickness may vary depending on the developing processing.

Silver halide emulsions are usually subjected to physical ripening, chemical ripening, and spectral sensitization. Additives which can be used in these steps are described in RD, Nos. 17643, 18716, and 307105, as hereinafter listed.

In the light-sensitive material of the present invention, a mixture of two or more light-sensitive emulsions differing in at least one of characteristics including grain size, grain size distribution, halogen composition, crystal form, and sensitivity can be used in the same layer.

Surface-fogged silver halide grains as described in U.S. Pat. No. 4,082,553, inside-fogged silver halide grains as described in U.S. Pat. No. 4,626,498 and JP-A-59-214852, and colloidal silver can be preferably used in light-sensitive silver halide emulsion layers and/or substantially light-insensitive hydrophilic colloidal layers. The terminology "inside- or surface-fogged silver halide grains" as used herein means silver halide grains which are evenly (non-imagewise) developable, exposed or unexposed, without distinction. Methods for preparing inside- or surface-fogged silver halide grains are described in U.S. Pat. No. 4,626,498 and JP-A-59-214852.

In the inside-fogged core/shell type silver halide grains, the core and the outer shell may have either the same or different halogen composition.

The inside- or surface-fogged silver halide grains may have any halogen composition selected from silver chloride, silver chlorobromide, silver iodobromide, and silver chloroiodobromide. While these fogged silver halide grains are not particularly limited in grain size, a preferred mean grain size is from 0.01 to 0.75 μm, particularly from 0.05 to 0.6 μm. The fogged silver halide grains are not particularly limited in crystal form, either regular or irregular. A poly-dispersed emulsion can be used, but a mono-dispersed emulsion in which at least 95% of the total weight or number of silver halide grains have a grain size falling within 40% of a mean grain size is preferred.

In the present invention, light-insensitive silver halide fine grains can be preferably used. The terminology "light-insensitive silver halide fine grains" as used herein means silver halide fine grains which are not sensitive to light from imagewise exposure for obtaining a color image and are therefore not substantially developed during development processing. It is preferable that the light-insensitive silver halide fine grains are not previously fogged.

The silver halide fine grains have a silver bromide content of from 0 to 100 mol % and may contain, if desired, silver chloride and/or silver iodide, preferably at a silver iodide content of from 0.5 to 10 mol %.

The silver halide fine grains preferably have a mean grain size (an average circle-equivalent diameter of the projected area) of from 0.01 to 0.5 μm, more preferably from 0.02 to 0.2 μm.

The silver halide fine grains can be prepared in the same manner as for general light-sensitive silver halide grains. The surface of the silver halide fine grains needs to be neither optically sensitized nor spectrally sensitized. It is desirable, however, that a known stabilizer, such as triazole compounds, azaindene compounds, benzothiazolium compounds, mercapto compounds, and zinc compounds, be added before the silver halide fine grains are added to a coating composition. The layer containing the silver halide fine grains preferably contains colloidal silver.

The light-sensitive material of the present invention preferably has a silver coverage of not more than 6.0 g/m², more preferably not more than 4.5 g/m².

Known photographic additives which can be used in the present invention are described in RD, Nos. 17643, 18716, and 307105, supra, as shown below.

| Additive | RD 17643 | RD 18716 | RD 307105 |
|---|---|---|---|
| 1. Chemical Sensitizer | p. 23 | p. 648, right column (RC) | p. 866 |
| 2. Sensitivity Increasing Agent | | p. 648, RC | |
| 3. Spectral Sensitizer, Supersensitizer | pp. 23–24 | p. 648, RC to p. 649, RC | pp. 866–868 |
| 4. Brightening Agent | p. 24 | p. 647, RC | p. 868 |
| 5. Antifoggant, Stabilizer | pp. 24–25 | p. 649, RC | pp. 868–870 |
| 6. Light Absorber, Filter Dye, Ultraviolet Absorber | pp. 25–26 | p. 649, RC to p. 650, left column (LC) | p. 873 |
| 7. Stain Inhibitor | p. 24, RC | p. 650, LC to RC | p, 872 |
| 8. Dye Image Stabilizer | p. 25 | p. 650, LC | p. 872 |
| 9. Hardening Agent | p. 26 | p. 651, LC | pp. 874–875 |
| 10. Binder | p. 26 | p. 651, LC | pp. 873–874 |
| 11. Plasticizer, Lubricant | p. 27 | p. 650, RC | p. 876 |
| 12. Coating Aid, Surface Active Agent | pp. 26–27 | p. 650, RC | pp. 875–876 |
| 13. Antistatic Agent | p. 27 | p. 650, RC | pp. 876–877 |
| 14. Matting Agent | | | pp. 878–879 |

In order to prevent deterioration in photographic performance due to formaldehyde gas, a compound capable of reacting with formaldehyde to fix it as described in U.S. Pat. Nos. 4,411,987 and 4,435,503 is preferably added to the light-sensitive materials.

The light-sensitive material of the invention preferably contains the mercapto compound described in U.S. Pat. Nos. 4,740,454 and 4,788,132, JP-A-62-18539, and JP-A-1-283551.

The light-sensitive material preferably contains a compound capable of releasing a fogging agent, a development accelerator, a silver halide solvent, or a precursor thereof regardless of the amount of developed silver produced by development processing, as described in JP-A-1-106052.

The light-sensitive material preferably contains the dye dispersion described in WO 88/04794 and JP-A-1-502912 or the dye described in EP 317,308A, U.S. Pat. No. 4,420,555 and JP-A-1-259358.

Various couplers can be used in the present invention. Specific examples of useful couplers are described in patents cited in RD, No. 17643, VII-C to G, and RD, No. 307105, VII-C to G.

Examples of suitable yellow couplers are described, e.g., in U.S. Pat. Nos. 3,933,501, 4,022,620, 4,326,024, 4,401,752, and 4,248,961, JP-B-58-10739, British Patents 1,425,020 and 1,476,760, U.S. Pat. Nos. 3,973,968, 4,314,023, and 4,511,649, and EP 249,473A.

Examples of suitable magenta couplers include 5-pyrazolone couplers and pyrazoloazole couplers. Examples of particularly preferred magenta couplers are described in U.S. Pat. Nos. 4,310,619 and 4,351,897, European Patent 73,636, U.S. Pat. Nos. 3,061,432 and 3,725,067, RD No. 24220 (Jun., 1984), JP-A-60-33552, RD No. 24230 (Jun., 1984), JP-A-60-43659, JP-A-61-72238, JP-A-60-35730, JP-A-55-118034, JP-A-60-185951, U.S. Pat. Nos. 4,500,630, 4,540,654, and 4,556,630, and WO 88/04795.

Cyan couplers include phenol couplers and naphthol couplers. Examples of suitable couplers are described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Patent Publication No. 3,329,729, EP 121,365A, EP 249,453A, U.S. Pat. Nos. 3,446,622, 4,333,999, 4,775,616, 4,451,559, 4,427,767, 4,690,889, 4,254,212, and 4,296,199, and JP-A-61-42658. Pyrazoloazole type couplers described in JP-A-64-553, JP-A-64-554, JP-A-64-555, and JP-A-64-556 and imidazole type couplers described in U.S. Pat. No. 4,818,672 may also be used.

Typical examples of polymerized dye-forming couplers are described in U.S. Pat. Nos. 3,451,820, 4,080,211, 4,367,282, 4,409,320, and 4,576,910, British Patent 2,102,137, and EP 341,188A.

Examples of suitable couplers which develop a dye having moderate diffusibility are described in U.S. Pat. No. 4,366,237, British Patent 2,125,570, European Patent 96,570, and West German Patent (OLS) No. 3,234,533.

Examples of suitable colored couplers which can be used for correcting unnecessary absorption of a developed dye are described in RD, No. 17643, VII-G, ibid, No. 307105, VII-G, U.S. Pat. No. 4,163,670, JP-B-57-39413, U.S. Pat. Nos. 4,004,929 and 4,138,258 and British Patent 1,146,368. Further, couplers capable of releasing a fluorescent dye upon coupling with which unnecessary absorption of a developed dye is corrected as described in U.S. Pat. No. 4,774,181 and couplers having a dye precursor group as a releasable group which is capable of reacting with a developing agent to form a dye as described in U.S. Pat. No. 4,777,120 are preferably used.

Couplers capable of releasing a photographically useful group on coupling can also be used advantageously. Examples of suitable DIR couplers capable of releasing a development inhibitor, other than those represented by formula (I), are described in patents cited in RD, No. 17643, VII-F, ibid, No. 307105, VII-F, JP-A-57-151944, JP-A-57-154234, JP-A-60-184248, JP-A-63-37346, JP-A-63-37350, and U.S. Pat. Nos. 4,248,962 and 4,782,012.

Examples of suitable couplers which imagewise release a nucleating agent or a development accelerator at the time of development are described in British Patents 2,097,140 and 2,131,188, JP-A-59-157638, and JP-A-59-170840. Compounds capable of releasing a fogging agent, a development accelerator, a silver halide solvent, etc., upon an oxidation-reduction reaction with an oxidation product of a developing agent as described in JP-A-60-107029, JP-A-60-252340, and JP-A-1-44940 are also preferably used.

Additional examples of couplers which can be used in the light-sensitive material of the present invention include competing couplers as described in U.S. Pat. No. 4,130,427; polyequivalent couplers as described in U.S. Pat. Nos. 4,283,472, 4,338,393, and 4,310,618; couplers capable of releasing a DIR redox compound, couplers capable of releasing a DIR coupler, redox compounds capable of releasing a DIR coupler, or redox compounds capable of releasing a DIR redox compound as described in JP-A-60-185950 and JP-A-62-24252; couplers capable of releasing a dye which restores its color after release as described in EP 173,302A and EP 313,308A; couplers capable of releasing a bleaching accelerator as described in RD, Nos. 11449 and 24241 and JP-A-61-201247; couplers capable of releasing a ligand as described in U.S. Pat. No. 4,555,477; couplers capable of releasing a leuco dye as described in JP-A-63-75747; and couplers capable of releasing a fluorescent dye as described in U.S. Pat. No. 4,774,181.

These couplers are introduced into the photographic materials by various known dispersion methods. High-boiling organic solvents which are useful in an oil-in-water dispersion method are described, e.g., in U.S. Pat. No. 2,322,027. Specific examples of the high-boiling organic solvents having a boiling point of 175° C. or higher under atmospheric pressure are phthalic esters (e.g., dibutyl phthalate, dicyclohexyl phthalate, di-2-ethylhexyl phthalate, decyl phthalate, bis(2,4-di-t-amylphenyl) phthalate, bis(2,4-di-t-amylphenyl) isophthalate, bis(1,1-diethylpropyl) phthalate), phosphoric or phosphonic esters (e.g., triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate, di-2-ethylhexylphenyl phosphonate), benzoic acid esters (e.g., 2-ethylhexyl benzoate, dodecyl benzoate, 2-ethylhexyl p-hydroxybenzoate), amides (e.g., N,N-diethyldodecanamide, N,N-diethyllaurylamide, N-tetradecylpyrrolidone), alcohols or phenols (e.g., isostearyl alcohol, 2,4-di-t-amylphenol), aliphatic carboxylic acid esters (e.g., bis(2-ethylhexyl) sebacate, dioctyl azelate, glycerol tributyrate, isostearyl lactate, trioctyl citrate), aniline derivatives (e.g., N,N-dibutyl-2-butoxy-5-t-octylaniline), and hydrocarbons (e.g., paraffin, dodecylbenzene, diisopropylnaphthalane). Organic solvents having a boiling point of not lower than about 30° C., and preferably from 50° C. to about 160° C. may be used in combination as an auxiliary solvent. Typical examples of such are ethyl acetate, butyl acetate, ethyl propionate, methyl ethyl ketone, cyclohexanone, 2-ethoxyethyl acetate, and dimethylformamide.

With respect to a latex dispersion method, the steps involved, the effects, and specific examples of loadable latices are described in U.S. Pat. No. 4,199,363 and West German Patent (OLS) Nos. 2,541,274 and 2,541,230.

The color light-sensitive materials of the present invention preferably contain various antiseptics or anti-fungal agents, such as phenethyl alcohol 1,2-benzisothiazolin-3-one, n-butyl p-hydroxybenzoate, phenol, 4-chloro-3,5-dimethylphenol, 2-phenoxyethanol, 2-(4-thiazolyl)benzimidazole, etc. as described in JP-A-63-257747, JP-A-62-272248, and JP-A-1-80941.

The present invention can be applied to a wide variety of color light-sensitive materials, such as color negative films for general use or for movies, color reversal films for slides or TV, color papers, color positive films, and color reversal papers.

Examples of supports which can be suitably used in the color light-sensitive materials are described, e.g., in RD, No. 17643, p. 28, ibid, No. 18716, pp. 647 (right column) to 648 (left column), and ibid, No. 307105, p. 879.

In the color light-sensitive materials of the present invention, the hydrophilic colloidal layers on the side having emulsion layers preferably have a total film thickness of not more than 28 μm, more preferably not more than 23 μm, particularly preferably not more than 18 μm, most preferably not more than 16 μm, and a rate of swelling $T_{\frac{1}{2}}$ of not more than 30 seconds, more preferably not more than 20 seconds. The terminglogy "total film thickness" as used herein means the film thickness as measured after conditioning at 25° C. and a relative humidity of 55% for 2 days. The terminology "rate of swelling $T_{\frac{1}{2}}$" means the time required for a color light-sensitive material to be swollen to $\frac{1}{2}$ the saturated swollen thickness, the saturated swollen thickness being defined as 90% of the maximum swollen thickness which is reached when the color light-sensitive material is swollen with a color developing solution at 30° C. for 3 minutes and 15 seconds. The rate of swelling can be determined by methods known in the art using, for example, a swellometer of the type described in A. Green et al., Photographic Science and Engineering, Vol. 19, No. 2, pp. 124–129.

The rate of swelling $T_{\frac{1}{2}}$ can be controlled by adding a proper amount of a hardening agent for a gelatin binder or by varying aging conditions after coating.

Further, the light-sensitive material preferably has a degree of swelling of from 150 to 400%. The terminology "degree of swelling" as used herein means the value obtained from the maximum swollen film thickness as defined above according to the formula (maximum swollen film thickness−film thickness)/film thickness.

The light-sensitive material of the present invention preferably has at least one hydrophilic colloidal layer called a backing layer having a total dry thickness of from 2 to 20 μm on the side opposite to the emulsion layer side. The backing layers preferably contain the above-described additives, e.g., light absorbents, filter dyes, ultraviolet absorbents, anti-static agents, hardening agents, binders, plasticizers, lubricants, coating aids, and surface active agents. The backing layers preferably have a degree of swelling of from 150 to 500%.

The above-described color photographic materials can be development processed according to usual methods as described in RD, No. 17643, pp. 28–29, ibid, No. 18716, p. 615, left to right columns, and ibid, No. 307105, pp. 880–881.

A color developing solution which can be used for development processing is preferably an alkaline aqueous solution containing an aromatic primary amine color developing agent. Useful color developing agents include aminophenol compounds and preferably p-phenylenediamine compounds. Typical examples of p-phenylenediamine compounds are 3-methyl-4-amino-N,N-diethylaniline, 3-methyl-4-amino-N-ethyl-N-ß-hydroxyethylamidoethylaniline, 3-methyl-4-amino-N-ethyl-β-methoxyethylaniline, and salts thereof (e.g., sulfates, hydrochlorides, and p-toluenesulfonates), with 3-methyl-4-amino-N-ethyl-N-β-hydroxyethylaniline sulfate being particularly preferred. These developing agents may be used either individually or in combination of two or more thereof, according to the purpose.

The color developing solution usually contains pH buffering agents (e.g., carbonates, borates or phosphates of alkali metals) and development inhibitors or antifoggants (e.g., chlorides, bromides, iodides, benzimidazoles, benzothiazoles, and mercapto compounds). If desired, the color developing solution further contains various preservatives, such as hydroxylamine, diethylhydroxylamine, sulfites, hydrazines (e.g., N,N-biscarboxymethylhydrazine), phenyl semicarbazides, triethanolamine, and catecholsulfonic acids; organic solvents, (e.g., ethylene glycol and diethylene glycol); development accelerators (e.g., benzyl alcohol, polyethylene glycol, quaternary ammonium salts, and amines); dye-forming couplers; competing couplers; auxiliary developing agents (e.g., 1-phenyl-3-pyrazolidone); viscosity-imparting agents; and various chelating agents, such as aminopolycarboxylic acids, aminopoly phosphonic acids, alkylphosphonic acids, and phosphonocarboxylic acids (e.g., ethylenediaminetetraacetic acid, nitrilotriacetic acid, ethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di-o-hydroxyphenylacetic acid, and salts thereof).

For reversal processing, color development is generally preceded by black-and-white (hereinafter abbreviated as B/W) development. A B/W developing solution to be used for B/W development contains one or more of known B/W developing agents, such as dihydroxybenzenes (e.g., hydroquinone), 3-pyrazolidones (e.g., 1-phenyl-3-pyrazolidone), and aminophenols (e.g., N-methyl-p-aminophenol).

The color or B/W developing solution generally has a pH between 9 and 12. The rate of replenishment for these developing solutions, though varying depending on the kind of color photographic material to be processed, is usually not more than 3 l per m$^2$ of a light-sensitive material. The rate of replenishment can be reduced to 500 ml/m$^2$ or less by reducing the bromide ion concentration in the replenisher. When processing is carried out at a reduced rate of replenishment, it is desirable to prevent evaporation and aerial oxidation of the processing solution by minimizing the contact area of the processing solution with air.

The contact area between a photographic processing solution and air can be expressed in terms of an opening ratio calculated by dividing the contact area (cm$^3$) of the processing solution with air by a volume (cm$^3$) of the processing solution. The opening ratio as defined above is preferably not more than 0.1, and more preferably between 0.001 and 0.05.

The opening ratio of the processing tank can be so adjusted by, for example, putting a barrier, such as a floating cover, on the liquid surface, using a movable cover as described in JP-A-1-82033, or utilizing slit development processing as described in JP-A-63-216050.

Reduction of the opening ratio is preferably applied not only to color development and B/W development but also to all the subsequent steps, such as the bleach, blix, fixing, washing, and stabilization steps.

Reduction of the replenishment rate may also be achieved by using a means for suppressing the accumulation of bromide ions in the developing solution.

The processing time with the color developing solution can be from 2 to 5 minutes. The processing time may be shortened by conducting development processing at an elevated temperature and an increased pH in an increased concentration of the color developing agent.

The photographic emulsion layers after color development are usually subjected to bleach. Bleach and fixing may be carried out either simultaneously (blix) or separately. For rapid processing, bleach may be followed by blix. Further, the mode of desilvering can be selected according to the end use. For example, blix may be effected using two tanks connected, or fixing may be followed by blix, or blix may be followed by bleach.

Bleaching agents to be used include compounds of polyvalent metals (e.g., iron (III)), peracids, quinones, and nitroso compounds. Typical bleaching agents include organic complex salts of iron (III), such as complex salts with aminopolycarboxylic acids (e.g., ethylenediaminetetraacetic acid, diethylenetriaminepentaacetic acid, cyclohexanediaminetetraacetic acid, methyliminodiacetic acid, 1,3-diaminopropanoltetraacetic acid, glycol ether diaminetetraacetic acid), citric acid, tartaric acid, or malic acid. Aminopolycarboxylic acid iron (III) complexes (e.g., (ethylenediaminetetraacetato)iron (III) salts and (1,3-diaminopropanetetraacetato)iron (III) salts). are preferred as bleaching agents from the standpoint of rapid processing and prevention of environmental pollution. Aminopolycarboxylic acid iron (III) complex salts are particularly useful either in a bleaching bath or in a blix monobath. A bleaching bath or blix bath containing these aminopolycarboxylic acid iron (III) complex salts usually has a pH between 4.0 and 8.0. A lower pH can also be employed for rapid processing.

If desired, a fixing bath, a blix bath, or a prebath thereof may contain known bleaching accelerators. Useful bleaching accelerators include compounds having a mercapto group or a disulfide group as described in U.S. Pat. No. 3,893,858, German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, and RD, No. 17129 (Jul., 1978); thiazolidine derivatives as described in JP-A-50-140129; thiourea derivatives as described in JP-B-45-8506, JP-A-52-20832, JP-A-53-32735, and U.S. Pat. No. 3,706,561; iodides as described in West German Patent 1,127,715 and JP-A-58-16235; polyoxyethylene compounds as described in German Patents 966,410 and 2,748,430; polyamine compounds as described in JP-B-45-8836; compounds as described in JP-A-49-40943, JP-A-49-59644, JP-A-53-94927, JP-A-54-35727, JP-A-55-26506, and JP-A-58-163940; and bromide ions. Among these bleaching accelerators, compounds having a mercapto group or a disulfide group are preferred because of their high accelerating effect. The compounds disclosed in U.S. Pat. No. 3,893,858, West German Patent 1,290,812, and JP-A-53-95630 are particularly preferred. In addition, the compounds disclosed in U.S. Pat. No. 4,552,834 are also preferred. These bleaching accelerators may be incorporated into a light-sensitive material. The bleaching accelerators are particularly effective for blix of color light-sensitive materials used in camera.

For the purpose of preventing bleach stain, the bleaching or blix bath preferably contains organic acids. Particularly preferred organic acids used to achieve this effect are those having an acid dissociation constant (pKa) of from 2 to 5 (e.g., acetic acid, propionic acid, and hydroxyacetic acid).

Fixing agents which can be used in a fixing or blix bath include thiosulfates, thiocyanates, thioether compounds, thioureas, and a large quantity of an iodide, with thiosulfates being commonly employed. In particular, ammonium thiosulfate is highly useful. The combined use of a thiosulfate and a thiocyanate, a thioether compound, a thiourea, etc., is also preferred. Preservatives for the fixing or blix bath preferably include sulfites, bisulfites, carbonyl-bisulfite adducts, and sulfinic acid compounds described in EP 294769A.

The fixing or blix bath preferably contains various aminopolycarboxylic acids or organophosphonic acids for stabilization.

Further, the fixing or blix bath preferably contains 0.1 to 10 mol/l of compounds having a pKa of from 6.0 to 9.0 for pH adjustment, preferably imidazoles (e.g., imidazole, 1-methylimidazole, 1-ethylimidazole, and 2-methylimidazole).

The total desilvering time is preferably as short as possible, as long as insufficient desilvering does not result. A preferred desilvering time is from 1 to 3 minutes, more preferably from 1 to 2 minutes. The desilvering temperature is from 25° to 50° C., preferably from 35° to 45° C. In the preferred temperature range, the rate of desilvering is improved, and stain formation after processing is effectively prevented.

It is desirable that desilvering should be performed while reinforcing stirring as much as possible. Methods or means for achieving reinforced stirring include a method in which a jet stream of a processing solution is made to strike against the surface of the emulsion layer as described in JP-A-62-183460; a method of using a rotating means to enhance stirring effects as described in JP-A-62-183461; a method in which a light-sensitive material is moved with its emulsion surface being in contact with a wire blade placed in a processing solution to create turbulence; and a method of increasing the total flow of a circulating processing solution. These stirring means are effective in any of a bleaching bath, a blix bath and a fixing bath. Reinforced stirring appears to accelerate supply of the bleaching agent or the fixing agent to emulsion layers and, as a result, to increase the rate of desilvering.

The above-described means for reinforced stirring is more effective in the case where a bleaching accelerator is used, markedly enhancing acceleration effects and eliminating the fixing inhibitory effect of the bleaching accelerator.

An automatic developing machine which can be used for processing the light-sensitive material preferably has a means for carrying a light-sensitive material as described in JP-A-60-191257, JP-A-60-191258, and JP-A-60-191259. As mentioned in JP-A-60-191257, supra, such a carrying means is highly effective to considerably reduce carry-over of the processing solution from a prebath into a succeeding bath, thereby preventing reduction of processing capacity. This means is particularly effective for reduction of the processing time or replenishment rate in each processing step.

The silver halide color light-sensitive material after desilvering is generally subjected to washing and/or stabilization.

The amount of washing water to be used in the washing step is selected from a broad range depending on characteristics of the light-sensitive material (e.g., the kind of components in the photographic materials, such as couplers), the end use of the light-sensitive material, the temperature of the washing water, the number of washing tanks (the number of stages), the replenishing system (e.g., counter-flow system or direct-flow system), and other various conditions. For example, a relation between the number of washing tanks and the quantity of water in a multi-stage counter-flow system can be obtained by the method described in *Journal of the Society of Motion Picture and Television Engineers*, Vol. 64, pp. 248-253 (May, 1955).

According to the disclosed multi-stage counterflow system, the required amount of water can be greatly reduced. However, bacteria tend to grow in the tank with an increase in water retention time, and suspended bacterial cells adhere to light-sensitive materials. Such a problem can be effectively addressed by adopting a method of reducing the amount calcium and magnesium ions in the washing water as described in JP-A-62-288838. It is also effective to use bactericides, such as isothiazolone compounds or thiabendazole compounds as described in JP-A-57-8542; chlorine-type bactericides (e.g., chlorinated sodium isocyanurate); and bactericides described in Horiguchi Hiroshi, *Bokin Bobaizai no Kagaku*, (Sankyo Shuppan, 1986), Eisei Gijutsukai (ed.), *Biseibutsu no Mekkin, Sakkin, Bobai Gijutsu*, (Kogyo Gijutsukai, 1982), and Nippon Bokin Bobai Gakkai (ed.), *Bokin Bobaizai Jiten* (1986) (e.g., benzotriazole)

Washing water usually has a pH between 4 and 9, preferably between 5 and 8. Washing conditions, though varying depending on the characteristics or the end use of the light-sensitive material and the like, are usually from 15° to 45° C. in temperature and from 20 seconds to 10 minutes in time, preferably from 25° to 40° C. in temperature and from 30 seconds to 5 minutes in time.

The washing step may be replaced with stabilization processing step. Where stabilization is conducted in place of washing, any of known stabilizing techniques described (e.g., in JP-A-57-8543, JP-A-58-14834, and JP-A-60-220345) can be utilized. Where washing is followed by stabilization, the stabilizing bath to be used includes a solution containing a dye stabilizer and a surface active agent, which is used as a final bath for color light-sensitive materials for shooting. Suitable dye stabilizers include aldehydes (e.g., formalin and glutaraldehyde), N-methylol compounds, hexamethylenetetramine, and an aldehydesulfite adduct. If desired, the stabilizing bath may also contain various chelating agents and antifungal agents.

The overflow accompanying replenishment for washing and/or stabilization may be reused in other processing steps, such as a desilvering step.

In cases where each processing solution is concentrated by vaporization during processing with an automatic developing machine, water is preferably supplied to the processing solution for correction of the concentration.

For the purpose of simplifying the processing and enhancing the processing speed, the silver halide color light-sensitive material may contain therein a color developing agent, preferably in the form of a precursor thereof. Examples of color developing agent precursors include indoaniline compounds described in U.S. Pat. No. 3,342,597, Schiff base compounds described in U.S. Pat. No. 3,342,599 and RD, Nos. 14850 and 15159, aldol compounds described in RD, No. 13924, metal complex salts described in U.S. Pat. No. 3,719,492, and urethane compounds described in JP-A-53-135628.

If desired, the silver halide color light-sensitive material may further contain therein various 1-phenyl-3-pyrazolidone compounds for the purpose of accelerating color development. Typical examples of these accelerators are described in JP-A-56-64339, JP-A-57-144547, and JP-A-58-115438.

Each of the above-described processing solutions is used at a temperature of from 10° to 50° C. and, in a standard manner, from 33° C. to 38° C. Higher processing temperatures may be employed for reducing processing time, or lower temperatures may be employed for improving image quality or stability of the processing solution.

The prevent invention is also applicable to heat-developable light-sensitive materials described in U.S. Pat. No. 4,500,626, JP-A-60-133449, JP-A-59-218443, JP-A-61-238056, and EP 210,660A2.

The present invention is now illustrated in greater detail by way of the following examples, but it should be understood that the present invention is not deemed to be limited thereto. All parts, percents and ratios are by weight unless otherwise indicated.

EXAMPLE 1

The following layers were coated on a triacetyl cellulose film support having a subbing layer to prepare a light-sensitive material (designated Sample 101).

| (1) | Emulsion Layer: | |
|---|---|---|
| | Tabular grain emulsion (AgI: 6 mol %; average aspect ratio: 7.5; mean grain size: 0.50 μm) | 2.50 g-Ag/m$^2$ |
| | Coupler (1) of the invention | 0.22 g/m$^2$ |
| | Tricresyl phosphate | 1.20 g/m$^2$ |
| | Gelatin | 3.80 g/m$^2$ |
| (2) | Protective Layer: | |
| | Sodium 2,4-dichloro-6-hydroxy-s-triazine | 0.10 g/m$^2$ |
| | Gelatine | 1.8 g/m$^2$ |

Samples 102 to 113 were prepared in the same manner as for Sample 101, except for replacing Coupler (1) with the equimolar amount of each of couplers shown in Table 1 below.

Each of Samples 101 to 113 was imagewise exposed to white light and subjected to color development processing according to the following procedure. The maximum yellow density of the processed sample was measured.

Then, the processed sample was divided into two pieces. One piece was allowed to stand at 60° C. and 70% RH (relative humidity) for 14 days (accelerated thermal deterioration test), and the other piece was allowed to stand under irradiation with a fluorescent lamp of 20,000 lux for 7 days (accelerated light deterioration test). The yellow density after the standing was measured.

The results obtained are shown in Table 1.

| Step | Time | Temp. |
|---|---|---|
| Color development | 3'15" | 38° C. |
| Bleach | 1'100" | 38° C. |
| Blix | 3'15" | 38° C. |
| Washing (1) | 40" | 35° C. |
| Washing (2) | 1'00" | 35° C. |
| Stabilization | 40" | 38° C. |
| Drying | 1'15" | 55° C. |

The processing solutions used in these steps had the following formulations.

| Color Developing Solution Formulation: | |
|---|---|
| Diethylenetriaminepentaacetic acid | 1.0 g |
| 1-Hydroxyethylidene-1,1-diphosphonic acid | 3.0 g |
| Sodium sulfite | 4.0 g |
| Potassium carbonate | 30.0 g |
| Potassium bromide | 1.4 g |
| Potassium iodide | 1.5 mg |
| Hydroxylamine sulfate | 2.4 g |
| 4-[N-Ethyl-N-β-hydroxyethylamino]-2- | 4.5 g |

-continued

| | |
|---|---|
| methylaniline sulfate | |
| Water to make | 1.0 l |
| pH | 10.05 |
| Bleaching Solution Formulation: | |
| Ammonium (ethylenediaminetetra-acetato)iron (III) dihydrate | 120.0 g |
| Disodium ethylenediaminetetraacetate | 10.0 g |
| Ammonium bromide | 100.0 g |
| Ammonium nitrate | 10.0 g |
| Bleaching accelerator: | 0.005 mol |

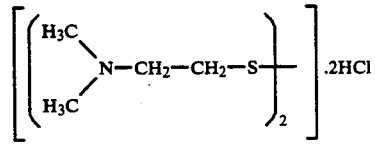

| | |
|---|---|
| Aqueous ammonia (27%) | 15.0 ml |
| Water to make | 1.0 l |
| pH | 6.3 |
| Blix Solution Formulation: | |
| Ammonium (ethylenediaminetetra-acetato)iron (III) dihydrate | 50.0 g |
| Disodium ethylenediaminetetraacetate | 5.0 g |
| Sodium sulfite | 12.0 g |
| Aqueous ammonium thiosulfate solution (70%) | 240.0 ml |
| Aqueous ammonia (27%) | 6.0 ml |
| Water to make | 1.0 l |
| pH | 7.2 |

Washing Water:

Tap water was passed through a mixed bed column packed with an H-type strongly acidic cation exchange resin ("Amberlite IR-120B" produced by Rohm & Hass) and an OH-type strongly basic anion exchange resin ("Amberlite IRA-400" produced by Rhom & Hass) to reduce the calcium ion and magnesium ion each to 3 mg/l or less, and to the thus treated water was added 20 mg/l of sodium dichloroisocyanburate and 150 mg/l of sodium sulfate. The resulting washing water had a pH between 67.5 and 7.5.

| Stabilizer Formulation: | |
|---|---|
| Formalin (37%) | 2.0 ml |
| Polyoxyethylene p-monononylphenyl ether (average degree of polymerization: 10) | 0.3 g |
| Disodium ethylenediaminetetraacetate | 0.05 g |
| Water to make | 1.0 l |
| pH | 5.0–8.0 |

TABLE 1

| Sample No. | Coupler | Maximum Density | Density After Accelerated Deterioration | |
|---|---|---|---|---|
| | | | Heat | Light |
| 101 (Invention) | (1) | 0.48 | 0.47 | 0.48 |
| 102 (Invention) | (2) | 0.50 | 0.48 | 0.50 |
| 103 (Invention) | (3) | 0.50 | 0.49 | 0.49 |
| 104 (Invention) | (4) | 0.49 | 0.48 | 0.49 |
| 105 (Invention) | (7) | 0.46 | 0.45 | 0.46 |
| 106 (Invention) | (10) | 0.48 | 0.46 | 0.48 |
| 107 (Invention) | (13) | 0.46 | 0.44 | 0.46 |
| 108 (Invention) | (16) | 0.47 | 0.45 | 0.46 |
| 109 (Invention) | (17) | 0.46 | 0.44 | 0.46 |
| 110 (Invention) | (22) | 0.48 | 0.47 | 0.47 |
| 111 (Comparison) | RC-1 | 0.49 | 0.15 | 0.10 |
| 112 (Comparison) | RC-2 | 0.02 | 0.01 | 0.02 |
| 113 (Comparison) | RC-3 | 0.05 | 0.02 | 0.02 |

Comparative couplers:
RC-1 (Coupler described in U.S. Pat. No. 4,477,563):

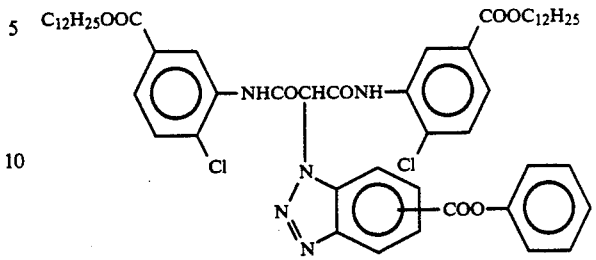

RC-2 (Coupler described in British Patent 1,204,680):

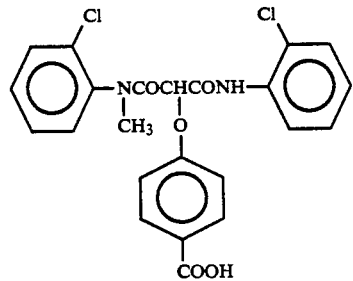

RC-3 (Coupler described in U.S. Pat. No. 4,149,886):

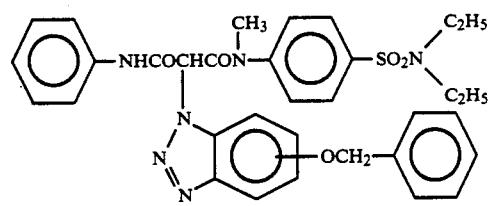

It can be seen from Table 1 that the comparative samples suffer from drawbacks, such as low developed color density or poor preservability of a developed dye image, whereas the samples using the coupler according to the present invention exhibit high color density and excellent dye image stability.

EXAMPLE 2

The following layers were coated on a triacetyl cellulose film support having a subbing layer to prepare a light-sensitive material (designated Sample 201).

| 1st Layer (Antihalation Layer): | |
|---|---|
| Black colloidal silver | 0.15 g-Ag/m$^2$ |
| Gelatin | 1.90 g/m$^2$ |
| ExM-8 | 2.0 × 10$^{-2}$ g/m$^2$ |
| 2nd Layer (Intermediate Layer): | |
| Gelatin | 2.10 g/m$^2$ |
| UV-1 | 3.0 × 10$^{-2}$ g/m$^2$ |
| UV-2 | 6.0 × 10$^{-2}$ g/m$^2$ |
| UV-3 | 7.0 × 10$^{-2}$ g/m$^2$ |
| ExF-1 | 4.0 × 10$^{-3}$ g/m$^2$ |
| Solv-2 | 7.0 × 10hu −2 g/m$^2$ |
| 3rd Layer (Low Sensitive Red-Sensitive Emulsion Layer): | |
| Silver iodobromide emulsion (AgI content: 2 mol %; high AgI inside type; sphere-equivalent diameter: 0.3 μm; coefficient of variation of sphere-equivalent diameter: 29%; regular crystals-twin mixed grains; aspect ratio: 2.5) | 0.50 g-Ag/m$^2$ |
| Gelatin | 1.50 g/m$^2$ |

-continued

| | |
|---|---|
| ExS-1 | $1.0 \times 10^{-4}$ mol/mol-AgX (X: halogen) |
| ExS-2 | $3.0 \times 10^{-4}$ mol/mol-AgX |
| EsS-3 | $1.0 \times 10^{-5}$ mol/mol-AgX |
| ExC-3 | $0.22$ g/m$^2$ |
| ExC-4 | $3.0 \times 10^{-2}$ g/m$^2$ |
| Solv-1 | $7.0 \times 10^{-3}$ g/m$^2$ |

4th Layer (Middle Sensitive Red-Sensitive Emulsion Layer):

| | |
|---|---|
| Silver iodobromide emulsion (AgI content: 4 mol %; high AgI inside type; sphere-equivalent diameter: 0.55 μm; coefficient of variation of sphere-equivalent diameter: 20%; regular crystals-twins mixed grains; aspect ratio: 1.0) | $0.85$ g-Ag/m$^2$ |
| Gelatin | $2.00$ g/m$^2$ |
| ExS-1 | $1.0 \times 10^{-4}$ mol/mol-AgX |
| ExS-2 | $3.0 \times 10^{-4}$ mol/mol-AgX |
| EsS-3 | $1.0 \times 10^{-5}$ mol/mol-AgX |
| ExC-2 | $8.0 \times 10^{-2}$ g/m$^2$ |
| ExC-3 | $0.33$ g/m$^2$ |
| ExY-13 | $2.0 \times 10^{-2}$ g/m$^2$ |
| ExY-14 | $1.0 \times 10^{-2}$ g/m$^2$ |
| Cpd-10 | $1.0 \times 10^{-4}$ g/m$^2$ |
| Solv-1 | $0.10$ g/m$^2$ |

5th Layer (High Sensitive Red-Sensitive Emulsion Layer):

| | |
|---|---|
| Silver iodobromide emulsion (AgI content: 10 mol %; high AgI inside type: sphere-equivalent diameter: 0.7 μm; coefficient of variation of sphere-equivalent diameter: 30%; regular crystals-twins mixed grains; aspect ratio: 2.0) | $0.70$ g-Ag/m$^2$ |
| Gelatin | $1.60$ g/m$^2$ |
| ExS-1 | $1.0 \times 10^{-4}$ mol/mol-AgX |
| ExS-2 | $3.0 \times 10^{-4}$ mol/mol-AgX |
| EsS-3 | $1.0 \times 10^{-5}$ mol/mol-AgX |
| ExC-5 | $7.0 \times 10^{-2}$ g/m$^2$ |
| ExC-6 | $8.0 \times 10^{-}$ g/m$^2$ |
| Solv-1 | $0.15$ g/m$^2$ |
| Solv-2 | $8.0 \times 10^{-2}$ g/m$^2$ |

6th Layer (Intermediate Layer):

| | |
|---|---|
| Gelatin | $1.10$ g/m$^2$ |
| P-2 | $0.17$ g/m$^2$ |
| Cpd-1 | $0.10$ g/m$^2$ |
| Cpd-4 | $0.17$ g/m$^2$ |
| Solv-1 | $5.0 \times 10^{-2}$ g/m$^2$ |

7th Layer (Low Sensitive Green-Sensitive Emulsion Layer):

| | |
|---|---|
| Silver iodobromide emulsion (AgI content: 2 mol %; high AgI inside type; sphere-equivalent diameter: 0.3 μm; coefficient of variation of sphere-equivalent diameter: 28%; regular crystals-twins mixed grains; aspect ratio: 2.5) | $0.30$ g-Ag/m$^2$ |
| Gelatin | $0.05$ g/m$^2$ |
| ExS-4 | $5.0 \times 10^{-4}$ mol/mol-AgX |
| ExS-5 | $2.0 \times 10^{-4}$ mol/mol-AgX |
| EsS-6 | $0.3 \times 10^{-4}$ mol/mol-AgX |
| ExM-8 | $1.0 \times 10^{-2}$ g/m$^2$ |
| ExM-9 | $0.20$ g/m$^2$ |
| ExY-13 | $3.0 \times 10^{-2}$ g/m$^2$ |
| Cpd-11 | $7.0 \times 10^{-3}$ g/m$^2$ |
| Solv-1 | $0.20$ g/m$^2$ |

8th Layer (Middle Sensitive Green-Sensitive Emulsion Layer):

| | |
|---|---|
| Silver iodobromide emulsion (AgI content: 4 mol %; high AgI inside type; sphere-equivalent diameter: 0.55 μm; coefficient of variation of sphere-equivalent diameter: 20%; regular crystals-twins mixed grains; aspect ratio: 4.0) | $0.70$ g-Ag/m$^2$ |
| Gelatin | $1.00$ g/m$^2$ |
| ExS-4 | $5.0 \times 10^{-4}$ mol/mol-AgX |
| ExS-5 | $2.0 \times 10^{-4}$ mol/mol-AgX |
| EsS-6 | $3.0 \times 10^{-5}$ mol/mol-AgX |
| ExM-8 | $1.5 \times 10^{-2}$ g/m$^2$ |
| ExM-9 | $0.15$ g/m$^2$ |
| ExM-10 | $1.0 \times 10^{-2}$ g/m$^2$ |
| ExM-11 | $0.10$ g/m$^2$ |
| ExY-13 | $4.0 \times 10^{-2}$ g/m$^2$ |
| Cpd-11 | $9.0$ g/m$^2$ |
| Solv-1 | $0.20$ g/m$^2$ |

9th Layer (High Sensitive Green-Sensitive Emulsion Layer):

| | |
|---|---|
| Silver iodobromide emulsion (AgI content: 10 mol %; high AgI inside type; sphere-equivalent diameter: 0.7 μm; coefficient of variation of sphere-equivalent diameter: 30%; regular crystals-twins mixed grains; aspect ratio: 2.0) | $0.50$ g-Ag/m$^2$ |
| Gelatin | $0.90$ g/m$^2$ |
| ExS-4 | $2.0 \times 10^{-4}$ mol/mol-AgX |
| ExS-5 | $2.0 \times 10^{-4}$ mol/mol-AgX |
| EsS-6 | $2.0 \times 10^{-5}$ mol/mol-AgX |
| ExS-7 | $3.0 \times 10^{-4}$ |
| ExM-8 | $1.0 \times 10^{-2}$ g/m$^2$ |
| ExM-11 | $6.0 \times 10^{-2}$ g/m$^2$ |
| ExM-12 | $2.0 \times 10^{-2}$ g/m$^2$ |
| ExM-13 | $1.0 \times 10^{-2}$ g/m$^2$ |
| Cpd-2 | $1.0 \times 10^{-2}$ g/m$^2$ |
| Cpd-9 | $2.0 \times 10^{-4}$ g/m$^2$ |
| Cpd-10 | $2.0 \times 10^{-4}$ g/m$^2$ |
| Solv-1 | $0.20$ g/m$^2$ |
| Solv-2 | $5.0 \times 10^{-2}$ g/m$^2$ |

10th Layer (Yellow Filter Layer):

| | |
|---|---|
| Gelatin | $0.90$ g/m$^2$ |
| Yellow colloidal silver | $5.0 \times 10^{-2}$ g/m$^2$ |
| Cpd-1 | $0.20$ g/m$^2$ |
| Solv-1 | $0.15$ g/m$^2$ |

11th Layer (Low Sensitive Blue-Sensitive Emulsion Layer):

| | |
|---|---|
| Silver iodobromide emulsion (AgI content: 4 mol %; high AgI inside type; sphere-equivalent diameter: 0.5 μm; coefficient of variation of sphere-equivalent diameter: 15%; octahedral grains) | $0.40$ g-Ag/m$^2$ |
| Gelatin | $1.50$ g/m$^2$ |
| ExS-8 | $2.0 \times 10^{-4}$ mol/mol-AgX |
| ExY-13 | $9.0 \times 10^{-2}$ g/m$^2$ |
| ExY-15 | $0.90$ g/m$^2$ |
| Cpd-2 | $1.0 \times 10^{-2}$ g/m$^2$ |
| Solv-1 | $0.30$ g/m$^2$ |

12th Layer (High Sensitive Blue-Sensitive Emulsion Layer):

| | |
|---|---|
| Silver iodobromide emulsion (AgI content: 10 mol %; high AgI inside type; sphere-equivalent diameter: 1.3 μm; coefficient of variation of sphere-equivalent diameter: 25%; regular crystals-twins mixed grains; aspect ratio: 4.5) | $0.50$ g-Ag/m$^2$ |
| Gelatin | $0.60$ g/m$^2$ |
| ExS-8 | $1.0 \times 10^{-4}$ mol/mol-AgX |
| ExY-15 | $0.12$ g/m$^2$ |
| Cpd-2 | $1.0 \times 10^{-3}$ g/m$^2$ |

| | |
|---|---|
| Solv-1 | $4.0 \times 10^{-2}$ g/m$^2$ |
| 13th Layer (1st Protective Layer): | |
| Silver iodobromide fine grains (mean grain size: 0.07 μm; AgI content: 1 mol %) | 0.20 g-Ag/m$^2$ |
| Gelatin | 0.80 g/m$^2$ |
| UV-2 | 0.10 g/m$^2$ |
| UV-3 | 0.10 g/m$^2$ |
| UV-4 | 0.20 g/m$^2$ |
| Solv-3 | $4.0 \times 10^{-2}$ g/m$^2$ |
| P-2 | $9.0 \times 10^{-2}$ g/m$^2$ |
| 14th Layer (2nd Protective Layer): | |
| Gelatin | 0.90 g/m$^2$ |
| B-1 (diameter: 1.5 μm) | 0.10 g/m$^2$ |
| B-2 (diameter: 1.5 μm) | 0.10 g/m$^2$ |
| B-3 | $2.0 \times 10^{-2}$ g/m$^2$ |

| | |
|---|---|
| H-1 | 0.40 g/m$^2$ |

In addition to the above-described additives, Cpd-3, Cpd-5, Cpd-6, Cpd-7, Cpd-8, P-1, W-1, W-2, and W-3 were added to the sample for improving preservability, processability, pressure resistance, antifungal properties, antimicrobial properties, antistatic properties, and coating properties.

Furtgher, n-propyl p-hydroxybenzoate, B-4, F-1, F-4, F-5, F-6, F-7, F-8, F-9, F-10, F-11, F-13, and an iron, lead, gold, platinum, iridium or rhodium salt were also used in the sample.

Structural formulae or chemical names of the additives used in the sample preparation are shown below.

UV-1:

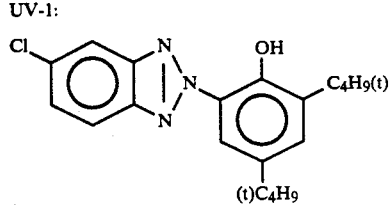

UV-2:

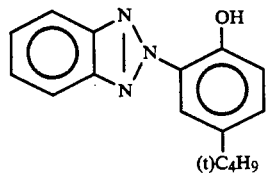

UV-3:

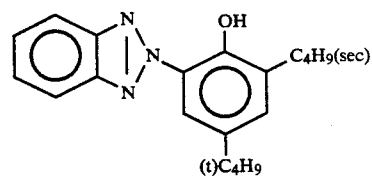

UV-4:

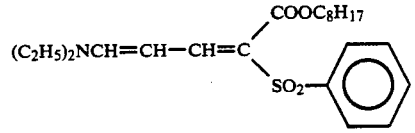

Solv-1:
Tricresyl phosphate
Solv-3:
Tri(2-ethylhexyl)phosphate

Solv-2:
Dibutyl phthalate
ExF-1:

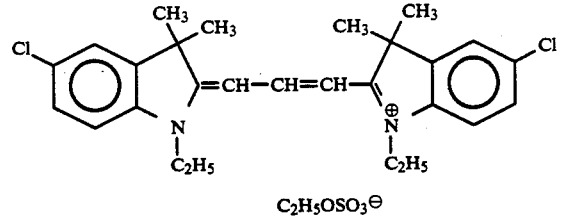

ExC-2:

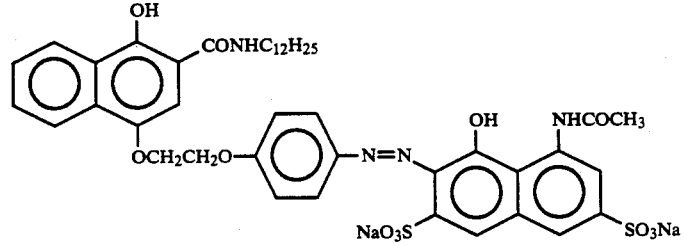

ExC-3:

ExC-4:

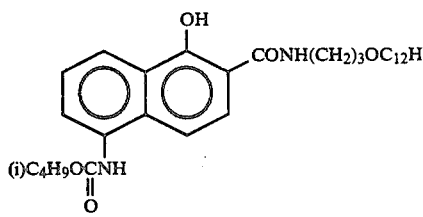
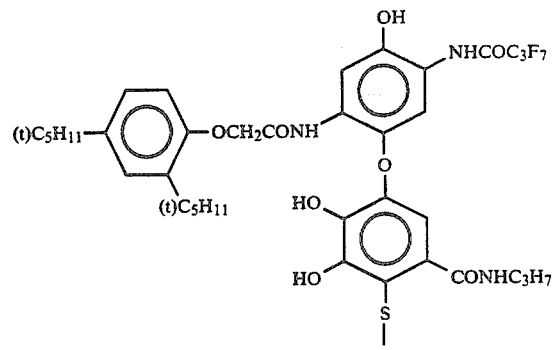
ExC-5:
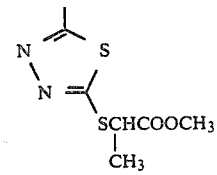
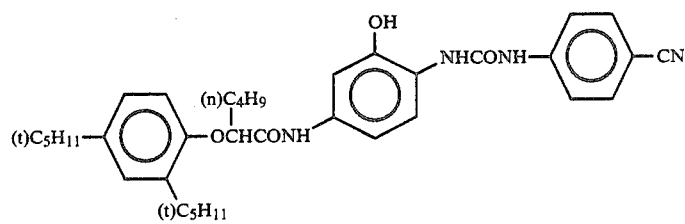
ExC-6:
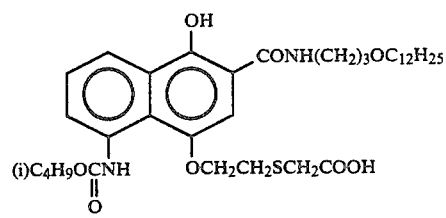
ExM-8:
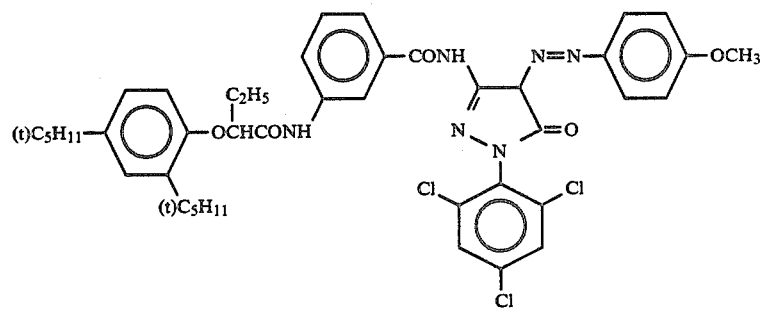
ExM-9:

-continued
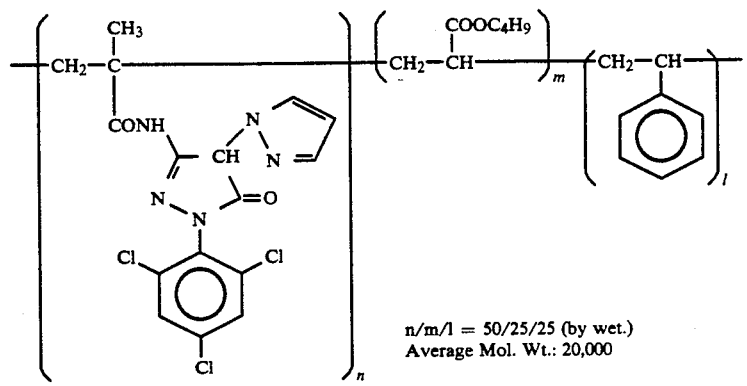
n/m/l = 50/25/25 (by wet.)
Average Mol. Wt.: 20,000
ExM-10:
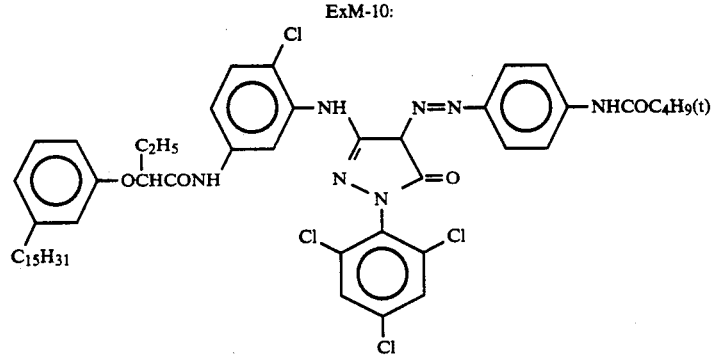
ExM-11:
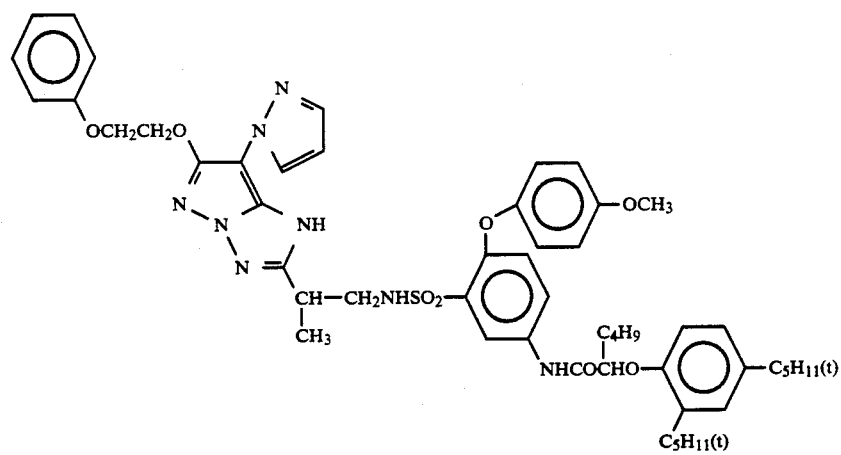
ExM-12:
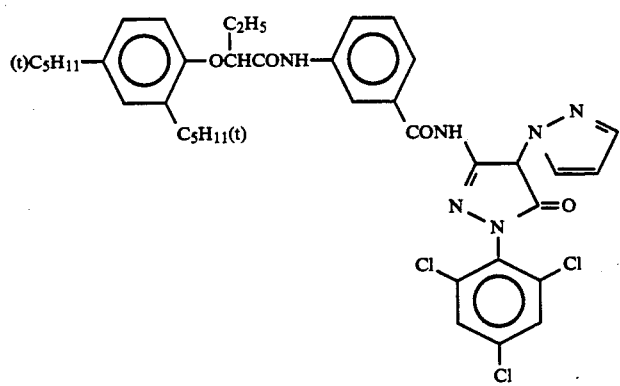
ExY-13 (Coupler described in U.S. Pat. No. 4,477,563):

-continued
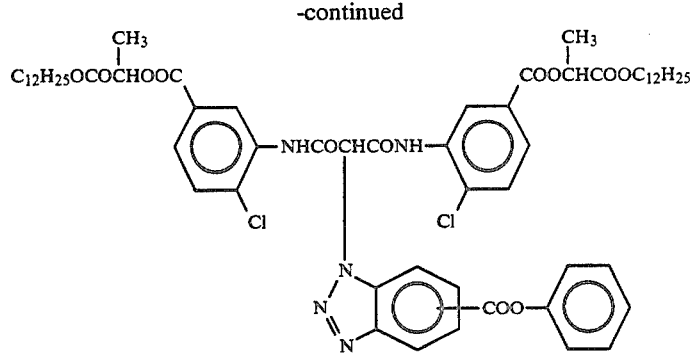
ExY-14:
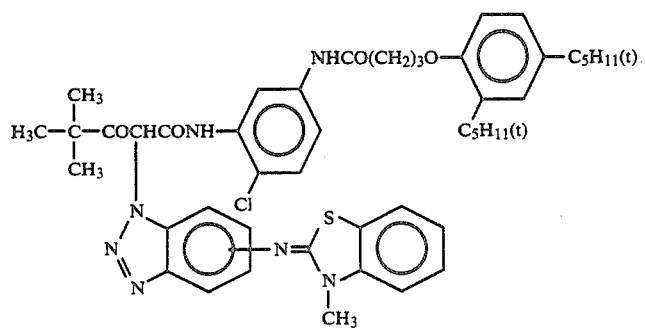
ExY-15:
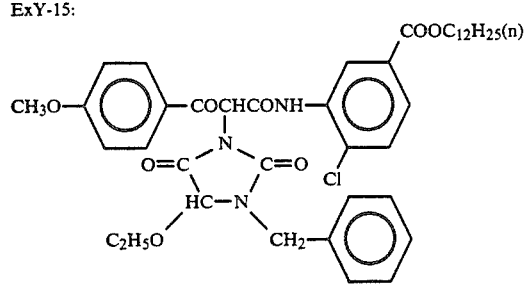
Cpd-1
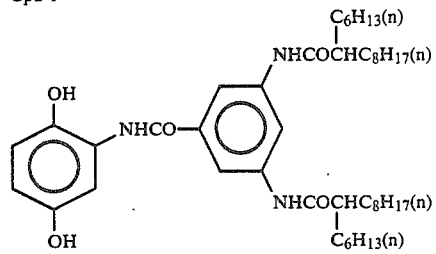
Cpd-2
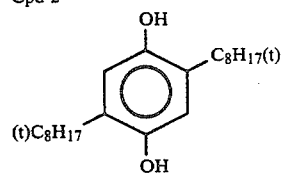
Cpd-3
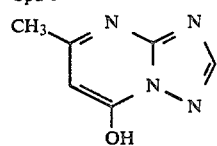
Cpd-4
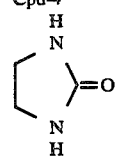
Cpd-5
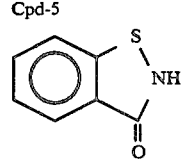
Cpd-6
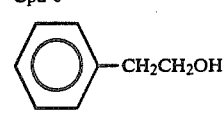
Cpd-7
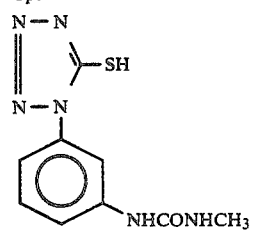
Cpd-8                                   Cpd-9

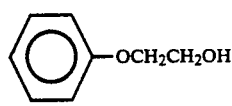
-continued
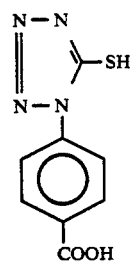
Cpd-10
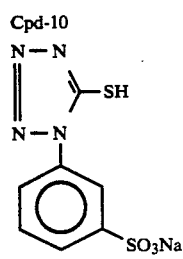
Cpd-11
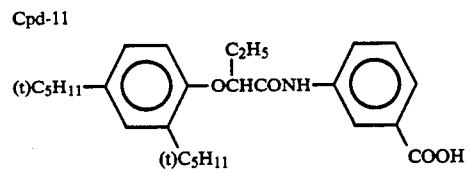
ExS-1
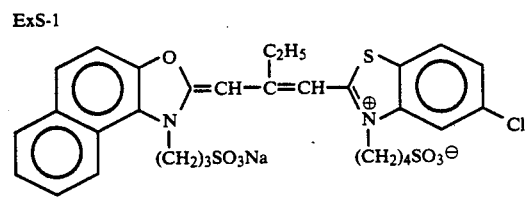
ExS-2
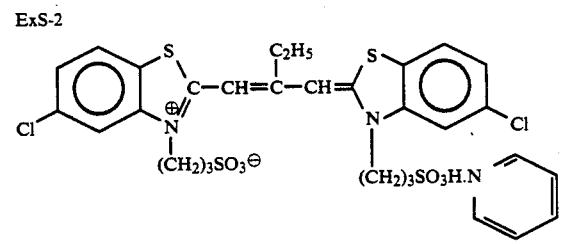
ExS-3
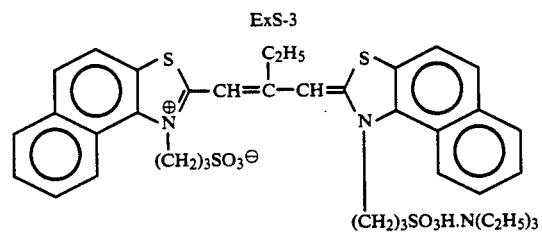
ExS-4
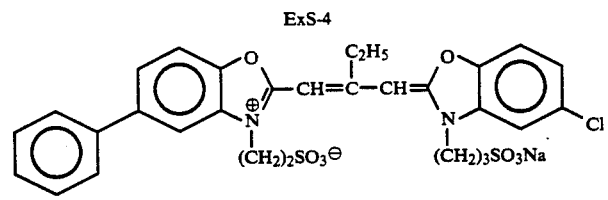
ExS-5
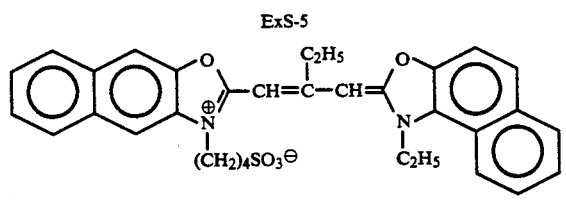
ExS-6
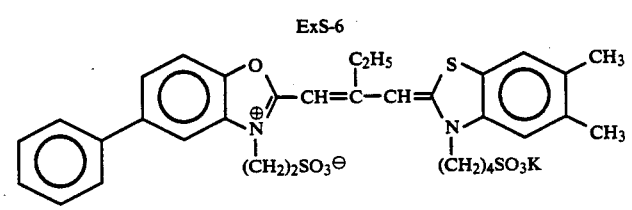
ExS-7

-continued
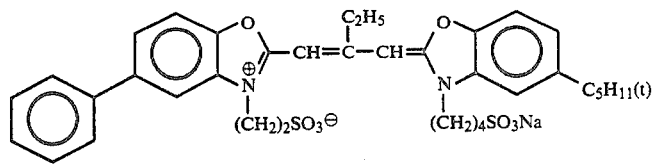
ExS-8
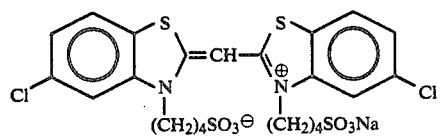
B-4
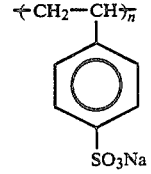
H-1
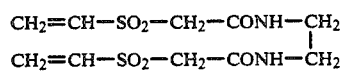
W-1
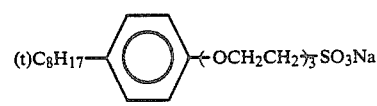
W-2
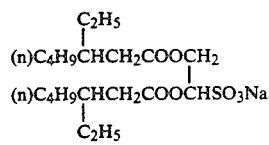
W-3
C$_8$F$_{17}$SO$_2$N(C$_3$H$_7$)CH$_2$COOK
P-1:
Vinylpyrrolidione-vinyl alcohol (70:30 by wt.) copolymer
P-2:
Polyethyl acrylate
F-1
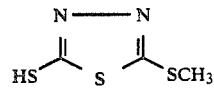
F-4
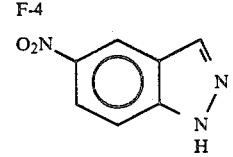
F-5
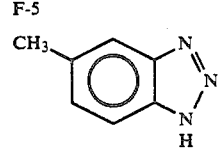
F-6
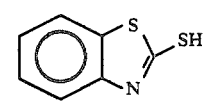
F-7
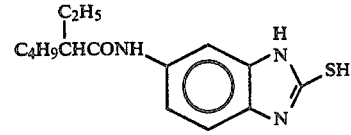
F-8
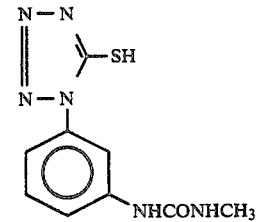
F-9
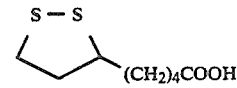
F-10
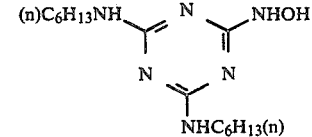
F-11
F-13

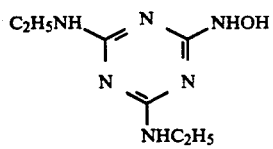

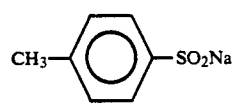

Samples 202 to 207 were prepared in the same manner as for Sample 201, except for replacing ExY-13 in the 4th, 7th, 8th, 9th, and 11th layer of Sample 201 with each of the couplers shown in Table 2 below at a ratio shown to the mole of ExY-13 in the corresponding layer (the amount of the coupler added was decided so that all the samples imagewise exposed to white light and processed as described below might have the same sensitivity and gamma as Sample 201).

Each of Samples 201 to 207 was imagewise exposed to green light and then processed according to the following procedure. A difference obtained by subtracting a yellow fog density from the yellow density at an area having a magenta density of fog+1.0 was taken as a degree of color contamination.

Further, each sample was imagewise exposed to white light, and then allowed to stand at 80° C. and 60% RH for 7 days (accelerated thermal deterioration test) or allowed to stand for 7 days with its emulsion layer side being irradiated with light (20,000 lux) of a fluorescent lamp (accelerated light deterioration test), and a decrease in yellow density at an area having an initial yellow density of 2.5 was measured. The results of these evaluations are shown in Table 2.

| Step | Processing Procedure: Time | Temp. | Rate of Replenishment* | Volume of Tank |
|---|---|---|---|---|
| Color development | 3'15" | 37.8° C. | 25 ml | 10 l |
| Bleach | 45" | 38.0° C. | 5 ml | 5 l |
| Fixing (1) | 45" | 38.0° C. | ** | 5 l |
| Fixing (2) | 45" | 38.0° C. | 30 ml | 5 l |
| Stabilization (1) | 20" | 38.0° C. | *** | 5 l |
| Stabilization (2) | 20" | 38.0° C. | *** | 5 l |
| Stabilization (3) | 20" | 38.0° C. | 40 ml | 5 l |
| Drying | 1' | 55° C. | | |

Note:
*Per meter of a 35 mm wide film
**Counter-flow system from fixing tank (2) to fixing tank (1).
***Counter-flow system from stabilization tank (3) to stabilization tank (1).

The amount of the developing solution which was carried over into the bleaching tank and the amount of the bleaching solution which was carried over into the stabilization tank was 2.5 ml and 2.0 ml, respectively, per m of a 35 wide film.

The processing solutions used had the following formulations.

| Color Developing Solution Formulation: | Running Solution (g) | Replenisher (g) |
|---|---|---|
| Diethylenetriaminepentaacetic acid | 5.0 | 6.0 |
| Sodium sulfite | 4.0 | 5.0 |
| Potassium carbonate | 30.0 | 37.0 |
| Potassium bromide | 1.3 | 0.5 |
| Potassium iodide | 1.2 mg | — |
| Hydroxylamine sulfate | 2.0 | 3.6 |
| 4-[N-Ethyl-N-β-hydroxyethyl-amino]-2-methylaniline sulfate | 4.7 | 6.2 |
| Water to make | 1.0 l | 1.0 l |
| pH | 10.00 | 10.15 |

| Bleaching Solution Formulation: | Running Solution (g) | Replenisher (g) |
|---|---|---|
| Ammonium (1,3-diaminopropane-tetraacetato)iron (III) monohydrate | 144.0 | 206.0 |
| 1,3-Diaminopropanetetraacetic acid | 2.8 | 4.0 |
| Potassium bromide | 84.3 | 120.0 |
| Ammonium nitrate | 17.5 | 25.0 |
| Aqueous ammonia (27%) | 10.0 | 1.8 |
| Acetic acid (98%) | 51.1 | 73.0 |
| Water to make | 1.0 l | 1.0 l |
| pH | 4.3 | 3.4 |

Fixing Solution Formulation:
The running solution and replenisher had the same composition.

| | |
|---|---|
| Disodium ethylenediaminetetraacetate | 1.7 g |
| Sodium sulfite | 14.0 g |
| Sodium bisulfite | 10.0 g |
| Aqueous ammonium thiosulfate solution (70 w/v%) | 210.0 ml |
| Ammonium thiocyanate | 163.0 g |
| Thiourea | 1.8 g |
| Water to make | 1.0 l |
| pH | 6.5 |

Stabilizer Formulation:
The running solution and replenisher had the same composition.

| | |
|---|---|
| Surface active agent: | 0.5 g |

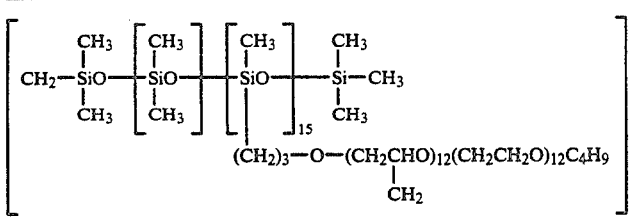

| | | | 0.4 g |
|---|---|---|---|
| Surface active agent: | | | |
| [C₁₀H₂₁—O—(CH₂CH₂O)₁₀—H] | | | |
| Triethanolamine | | | 2.0 g |
| 1,2-Benzisothiazolin-3-one methanol | | | 0.3 g |
| Formalin (37%) | | | 1.5 g |
| Water to make | | | 1.0 l |
| pH | | | 6.5 |

TABLE 2

| Sample No. | Coupler** Kind | Coupler** Amount* | Degree of Color Contamination | Decrease in Density Accelerated in Deterioration Test Heat | Decrease in Density Accelerated in Deterioration Test Light |
|---|---|---|---|---|---|
| 201 (Comparison) | ExY-13 | 1.0 | 0.06 | 0.25 | 0.21 |
| 202 (Comparison) | RC-3 | 13.0 | 0.25 | 0.18 | 0.17 |
| 203 (Comparison) | RC-5 | 4.0 | 0.12 | 0.16 | 0.14 |
| 204 (Invention) | (2) | 1.3 | 0.05 | 0.06 | 0.02 |
| 205 (Invention) | (18) | 1.0 | 0.04 | 0.06 | 0.02 |
| 206 (Invention) | (20) | 1.2 | 0.05 | 0.06 | 0.02 |
| 207 (Invention) | (4) | 1.5 | 0.05 | 0.08 | 0.03 |

Note:
*A molar ratio to ExY-13 used in Sample 201
**Coupler contained in the 7th, 8th and 9th layers.

Comparative Coupler:
RC-5 (Analogous to the coupler of U.S. Pat. No. 4,149,886):

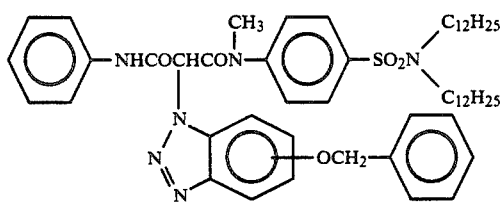

It can be seen from the results in Table 2 that the samples according to the present invention are suffer less from color contamination and have superior dye image stability because of the higher activity of their couplers used as compared with the comparative samples.

EXAMPLE 3

The following layers were coated on a 127 μm thick triacetyl cellulose film support having a subbing layer to prepare a multi-layer color light-sensitive material (designated Sample 301). The effect of the additives used herein is not limited to that described.

| 1st Layer (Antihalation Layer): | |
|---|---|
| Black colloidal silver | 0.25 g/m² |
| Gelatin | 1.9 g/m² |
| Ultraviolet absorbent (U-1) | 0.04 g/m² |
| Ultraviolet absorbent (U-2) | 0.1 g/m² |
| Ultraviolet absorbent (U-3) | 0.1 g/m² |
| Ultraviolet absorbent (U-4) | 0.1 g/m² |
| Ultraviolet absorbent (U-6) | 0.1 g/m² |
| High-boiling organic solvent (Oil-1) | 0.1 g/m² |
| 2nd Layer (Intermediate Layer): | |
| Gelatin | 0.40 g/m² |
| Compound (Cpd-D) | 10 mg/m² |
| High-boiling organic solvent (Oil-3) | 0.1 g/m² |
| Dye (D-4) | 0.4 mg/m² |
| 3rd Layer (Intermediate Layer): | |
| Surface- and inside-fogged silver iodobromide fine grains emulsion (mean grain size: 0.06 μm; coefficient of variation: 18%; AgI content: 1 mol %) | 0.05 g-Ag/m² |
| Gelatin | 0.4 g/m² |
| 4th Layer (Low Sensitive Red-Sensitive Emulsion Layer): | |
| Emulsion A | 0.2 g-Ag/m² |
| Emulsion B | 0.3 g-Ag/m² |
| Gelatin | 0.8 g/m² |
| Coupler (C-1) | 0.15 g/m² |
| Coupler (C-2) | 0.05 g/m² |
| Coupler (C-9) | 0.05 g/m² |
| Compound (Cpd-D) | 10 mg/m² |
| High-boiling organic solvent (Oil-2) | 0.1 g/m² |
| 5th Layer (Middle Sensitive Red-Sensitive Emulsion Layer): | |
| Emulsion B | 0.2 g-Ag/m² |
| Emulsion C | 0.3 g-Ag/m² |
| Gelatin | 0.8 g/m² |
| Coupler (C-1) | 0.2 g/m² |
| Coupler (C-2) | 0.05 g/m² |
| Coupler (C-3) | 0.2 g/m² |
| High-boiling organic solvent (Oil-2) | 0.1 g/m² |
| 6th Layer (High Sensitive Red-Sensitive Emulsion Layer): | |
| Emulsion D | 0.4 g-Ag/m² |
| Gelatin | 1.1 g/m² |
| Coupler (C-1) | 0.3 g/m² |
| Coupler (C-3) | 0.7 g/m² |
| Additive (P-1) | 0.1 g/m² |
| 7th Layer (Intermediate Layer): | |
| Gelatin | 0.6 g/m² |
| Additive (M-1) | 0.3 g/m² |
| Color mixing inhibitor (Cpd-K) | 2.6 mg/m² |
| Ultraviolet absorbent (U-1) | 0.1 g/m² |
| Ultraviolet absorbent (U-6) | 0.1 g/m² |
| Dye (D-1) | 0.02 g/m² |
| 8th Layer (Intermediate Layer): | |
| Surface- and inside-fogged silver iodobromide emulsion (mean grain size: 0.06 μm; coefficient of variation: 16%; AgI content: 0.3 mol %) | 0.02 g-Ag/m² |
| Gelatin | 1.0 g/m² |
| Additive (P-1) | 0.2 g/m² |
| Color mixing inhibitor (Cpd-J) | 0.1 g/m² |
| Color mixing inhibitor (Cpd-A) | 0.1 g/m² |
| 9th Layer (Low Sensitive Green-Sensitive Emulsion Layer): | |

| | | |
|---|---|---|
| Emulsion E | 0.3 g-Ag/m² | |
| Emulsion F | 0.1 g-Ag/m² | |
| Emulsion G | 0.1 g-Ag/m² | |
| Gelatin | 0.5 g/m² | |
| Coupler (C-7) | 0.05 g/m² | |
| Coupler (C-8) | 0.20 g/m² | |
| Compound (Cpd-B) | 0.03 g/m² | |
| Compound (Cpd-D) | 10 mg/m² | |
| Compound (Cpd-E) | 0.02 g/m² | |
| Compound (Cpd-F) | 0.02 g/m² | |
| Compound (Cpd-G) | 0.02 g/m² | |
| Compound (Cpd-H) | 0.02 g/m² | |
| High-boiling organic solvent (Oil-1) | 0.1 g/m² | |
| High-boiling organic solvent (Oil-2) | 0.1 g/m² | |
| 10th Layer (Middle Sensitive Green-Sensitive Emulsion Layer): | | |
| Emulsion G | 0.3 g-Ag/m² | |
| Emulsion H | 0.1 g-Ag/m² | |
| Gelatin | 0.6 g/m² | |
| Coupler (C-7) | 0.2 g/m² | |
| Coupler (C-8) | 0.1 g/m² | |
| Compound (Cpd-B) | 0.03 g/m² | |
| Compound (Cpd-E) | 0.02 g/m² | |
| Compound (Cpd-F) | 0.02 g/m² | |
| Compound (Cpd-G) | 0.05 g/m² | |
| Compound (Cpd-H) | 0.05 g/m² | |
| High-boiling organic solvent (Oil-2) | 0.01 g/m² | |
| 11th Layer (High Sensitive Green-Sensitive Emulsion Layer): | | |
| Emulsion I | 0.5 g-Ag/m² | |
| Gelatin | 1.0 g/m² | |
| Coupler (C-4) | 0.3 g/m² | |
| Coupler (C-8) | 0.1 g/m² | |
| Compound (Cpd-B) | 0.08 g/m² | |
| Compound (Cpd-E) | 0.02 g/m² | |
| Compound (Cpd-F) | 0.02 g/m² | |
| Compound (Cpd-G) | 0.02 g/m² | |
| Compound (Cpd-H) | 0.02 g/m² | |
| High-boiling organic solvent (Oil-1) | 0.02 g/m² | |
| High-boiling organic solvent (Oil-2) | 0.02 g/m² | |
| 12th Layer (Intermediate Layer): | | |
| Gelatin | 0.6 g/m² | |
| Dye (D-1) | 0.1 g/m² | |
| Dye (D-2) | 0.05 g/m² | |
| Dye (D-3) | 0.07 g/m² | |
| 13th Layer (Yellow Filter Layer): | | |
| Yellow colloidal silver | 0.1 g-Ag/m² | |
| Gelatin | 1.1 g/m² | |
| Color mixing inhibitor (Cpd-A) | 0.01 g/m² | |
| High-boiling organic solvent (Oil-1) | 0.01 g/m² | |
| 14th Layer (Intermediate Layer): | | |
| Gelatin | 0.6 g/m² | |
| 15th Layer (Low Sensitive Blue-Sensitive Emulsion Layer): | | |
| Emulsion J | 0.4 g-Ag/m² | |
| Emulsion K | 0.1 g-Ag/m² | |
| Emulsion L | 0.1 g-Ag/m² | |
| Gelatin | 0.8 g/m² | |
| Coupler (C-5) | 0.3 g/m² | |
| Compound (9) of the invention | 0.3 g/m² | |
| 16th Layer (Middle Sensitive Blue-Sensitive Emulsion Layer): | | |
| Emulsion L | 0.1 g-Ag/m² | |
| Emulsion M | 0.4 g-Ag/m² | |
| Gelatin | 0.9 g/m² | |
| Coupler (C-5) | 0.15 g/m² | |
| Coupler (C-6) | 0.15 g/m² | |
| Coupler (9) of the invention | 0.3 g/m² | |
| 17th Layer (High Sensitive Blue-Sensitive Emulsion Layer): | | |
| Emulsion N | 0.4 g-Ag/m² | |
| Gelatin | 1.2 g/m² | |
| Coupler (C-6) | 0.35 g/m² | |
| Coupler (9) of the invention | 0.35 g/m² | |
| 18th Layer (1st Protective Layer): | | |
| Gelatin | 0.7 g/m² | |
| Ultraviolet absorbent (U-1) | 0.04 g/m² | |
| Ultraviolet absorbent (U-2) | 0.01 g/m² | |
| Ultraviolet absorbent (U-3) | 0.03 g/m² | |
| Ultraviolet absorbent (U-4) | 0.03 g/m² | |
| Ultraviolet absorbent (U-5) | 0.05 g/m² | |
| Ultraviolet absorbent (U-6) | 0.05 g/m² | |
| High-boiling organic solvent (Oil-1) | 0.02 g/m² | |
| Formalin scavenger: | | |
| (Cpd-C) | 0.2 g/m² | |
| (Cpd-I) | 0.4 g/m² | |
| Dye (D-3) | 0.05 g/m² | |
| 19th Layer (2nd Protective Layer): | | |
| Colloidal silver | 0.1 mg-Ag/m² | |
| Silver iodobromide fine grains emulsion (mean grain size: 0.06 μm; AgI content: 1 mol %) | 0.1 g-Ag/m² | |
| Geltain | 0.4 g/m² | |
| 20th Layer (3rd Protective Layer): | | |
| Geltin | 0.4 g/m² | |
| Polymethyl methacrylate (average particle size: 1.5 μm) | 0.1 g/m² | |
| Methyl methacrylate-acrylic acid (4:6) copolymer (average particle size: 1.5 μm) | 0.1 g/m² | |
| Silicone oil | 0.03 g/m² | |
| Surface active agent (W-1) | 3.0 mg/m² | |
| Surface active agent (W-2) | 0.03 g/m² | |

Each of the emulsion layers further contained additives (F-1) to (F-8). Each layer further contained a gelatin hardening agent (H-1) and surface active agents (W-3) and (W-4) as coating aids or emulsifying agents. In addition, phenol, 1,2-benzisothiazolin-3-one, 2-phenoxyethanol, and phenethyl alcohol were added as antiseptics or antifungal agents.

Emulsions A to N used above are as follows.

| Emulsion No. | Grains | Mean Grain Size (μm) | Coefficient of Variation (%) | AgI Content (mol %) |
|---|---|---|---|---|
| A | Mono-dispersed tetradecahedral grains | 0.25 | 16 | 3.7 |
| B | Mono-dispersed cubic internal latent image type grains | 0.30 | 10 | 3.3 |
| C | Mono-dispersed tetradecahedral grains | 0.30 | 18 | 5.0 |
| D | Poly-dispersed twin grains | 0.60 | 25 | 2.0 |
| E | Mono-dispersed cubic grains | 0.17 | 17 | 4.0 |
| F | Mono-dispersed cubic grains | 0.20 | 16 | 4.0 |
| G | Mono-dispersed cubic internal latent image type grains | 0.25 | 11 | 3.5 |
| H | Mono-dispersed cubic internal latent image type grains | 0.30 | 9 | 3.5 |
| I | Poly-dispersed tabular grains (average aspect ratio: 4.0) | 0.80 | 28 | 1.5 |
| J | Mono-dispersed tetradecahedral grains | 0.30 | 18 | 4.0 |
| K | Mono-dispersed tetradecahedral grains | 0.37 | 17 | 4.0 |
| L | Mono-dispersed cubic internal latent image | 0.46 | 14 | 3.5 |

-continued

| Emulsion No. | Grains | Mean Grain Size (μm) | Coefficient of Variation (%) | AgI Content (mol %) |
|---|---|---|---|---|
| | type grains | | | |
| M | Mono-dispersed cubic grains | 0.55 | 13 | 4.0 |
| N | Poly-dispersed tabular grains (average aspect ratio: 7.0) | 1.00 | 33 | 1.3 |

Spectral Sensitization of Emulsions A to N

| Emulsion No. | Stabilizing Dye Kind | Amount (g/mol-AgX) | Stage of Adding Stabilizing Dye |
|---|---|---|---|
| A | S-1 | 0.025 | Immediately after chemical sensitization |
|   | S-2 | 0.25 | Immediately after chemical sensitization |
| B | S-1 | 0.01 | Immediately after grain formation |
|   | S-2 | 0.25 | Immediately after grain formation |
| C | S-1 | 0.02 | Immediately after chemical sensitization |
|   | S-2 | 0.25 | Immediately after chemical sensitization |
| D | S-1 | 0.01 | Immediately after chemical sensitization |
|   | S-2 | 0.10 | Immediately after chemical sensitization |
|   | S-7 | 0.01 | Immediately after chemical sensitization |
| E | S-3 | 0.5 | Immediately after chemical sensitization |
|   | S-4 | 0.1 | Immediately after chemical sensitization |
| F | S-3 | 0.3 | Immediately after chemical sensitization |
|   | S-4 | 0.1 | Immediately after chemical sensitization |
| G | S-3 | 0.25 | Immediately after grain formation |
|   | S-4 | 0.08 | Immediately after grain formation |
| H | S-3 | 0.2 | During grain formation |
|   | S-4 | 0.06 | " |
| I | S-3 | 0.3 | Immediately before the commencement of chemical sensitization |
|   | S-4 | 0.07 | Immediately before the commencement of chemical sensitization |
|   | S-8 | 0.1 | Immediately before the commencement of chemical sensitization |
| J | S-6 | 0.2 | During grain formation |
|   | S-5 | 0.05 | " |
| K | S-6 | 0.2 | " |
|   | S-5 | 0.05 | " |
| L | S-6 | 0.22 | Immediately after the completion of grain formation |
|   | S-5 | 0.06 | Immediately after the completion of grain formation |
| M | S-6 | 0.15 | Immediately after chemical sensitization |
|   | S-5 | 0.04 | Immediately after chemical sensitization |
| N | S-6 | 0.22 | Immediately after grain formation |
|   | S-5 | 0.06 | Immediately after grain formation |

Additives used in the sample preparation are shown below.

C-1

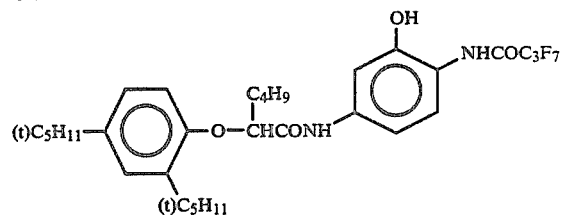

C-2

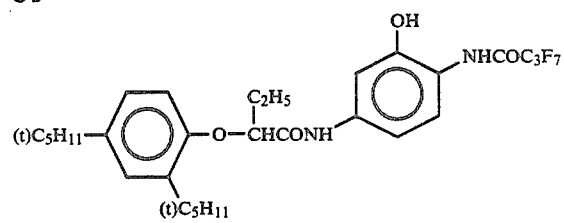

C-3

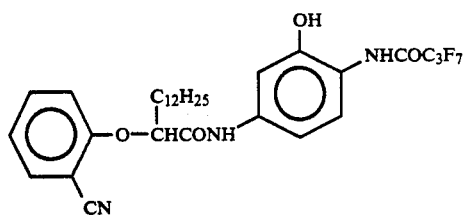
C-14
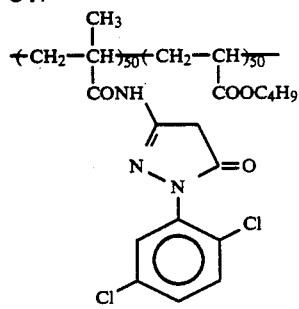
(copolymerization ratio: % by weight)
(average molecular weight: ca. 25,000)
C-5
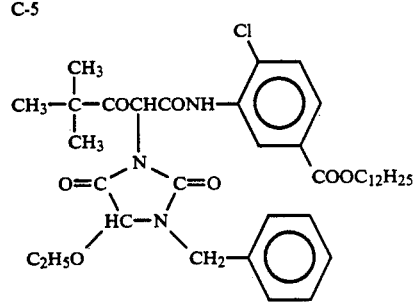
C-6
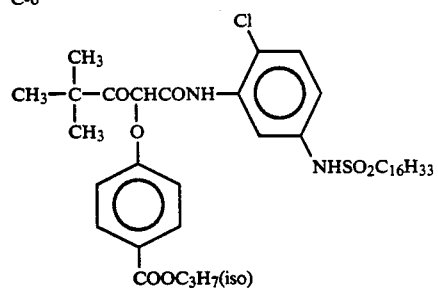
C-7
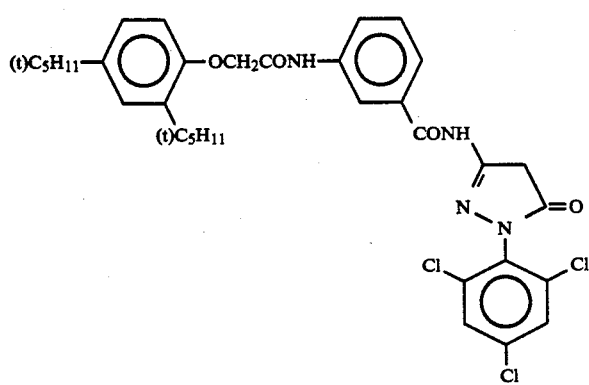
C-8

-continued
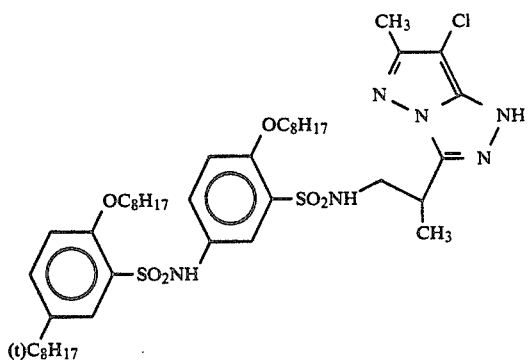
C-9
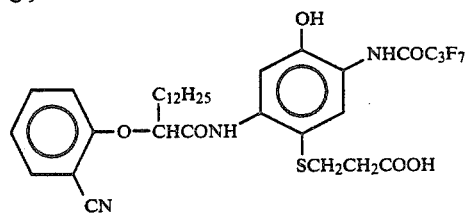
Oil-1:
Dibutyl phthalate
Oil-2:
Tricresyl phosphate
Oil-3:
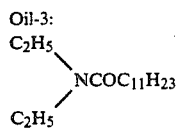
Cpd-A:
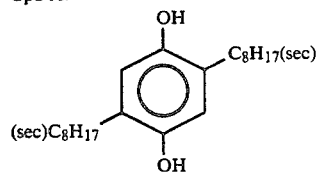
Cpd-B
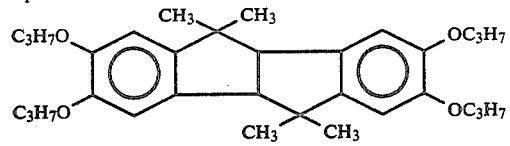
Cpd-C
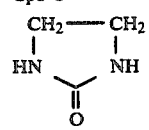
Cpd-D
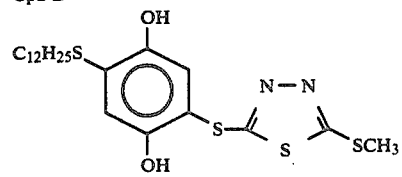
Cpd-E

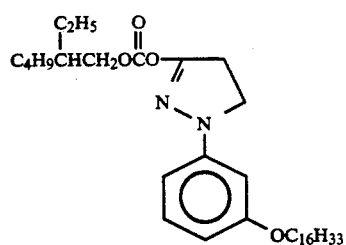
Cpd-F
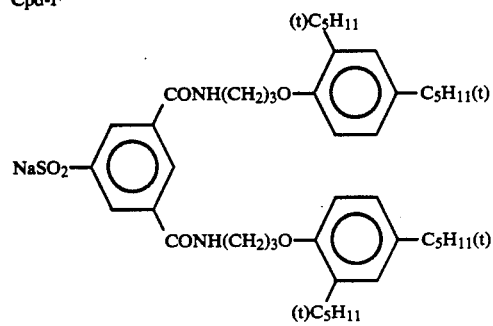
Cpd-G
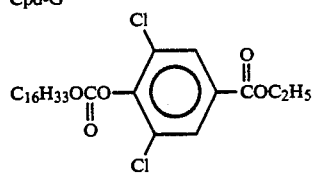
Cpd-H
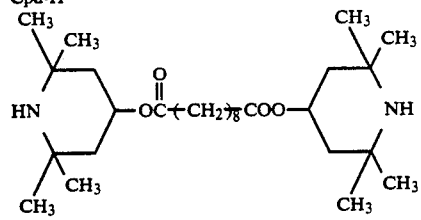
Cpd-I
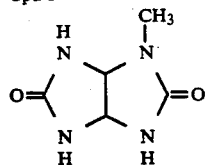
Cpd-J
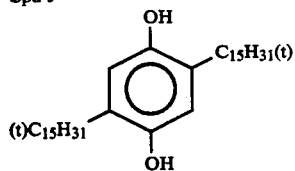
Cpd-K
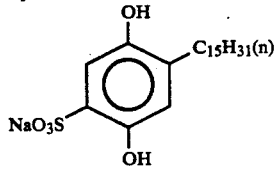
U-1

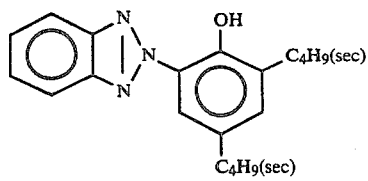
U-2
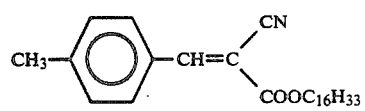
U-3
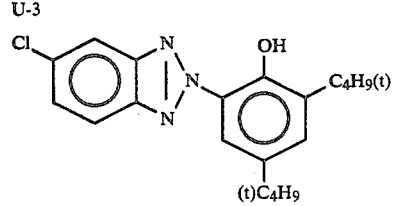
U-4
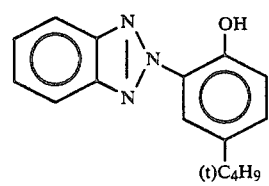
U-5
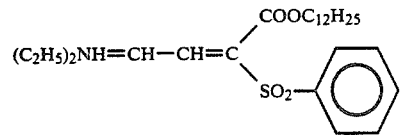
U-6
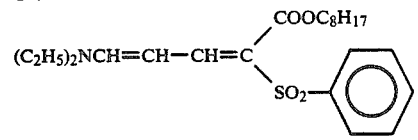
S-1
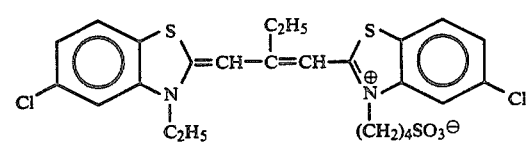
S-2
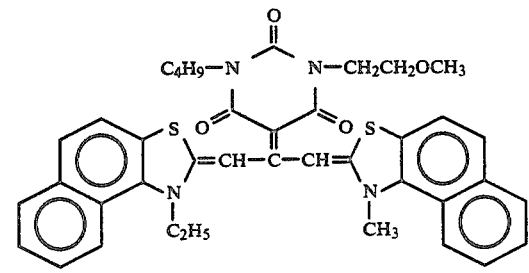
S-3

-continued
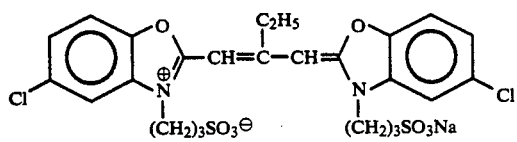
S-4
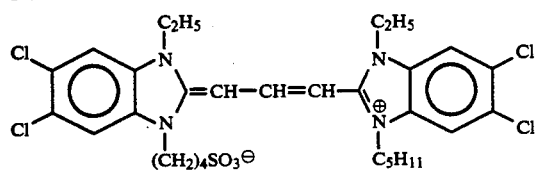
S-5
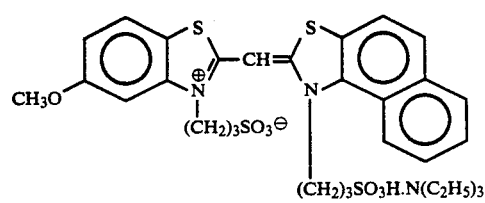
S-6
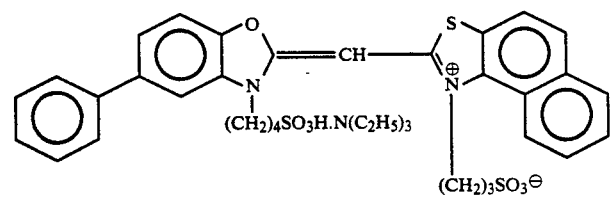
S-7
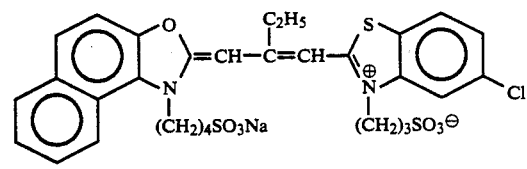
S-8
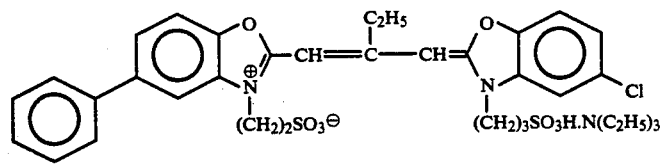
D-1
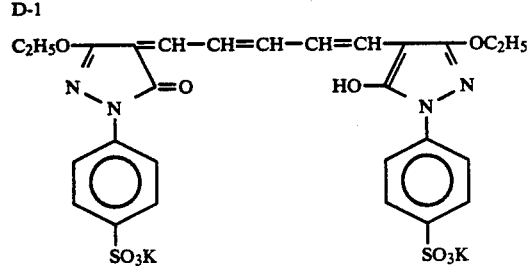
D-2

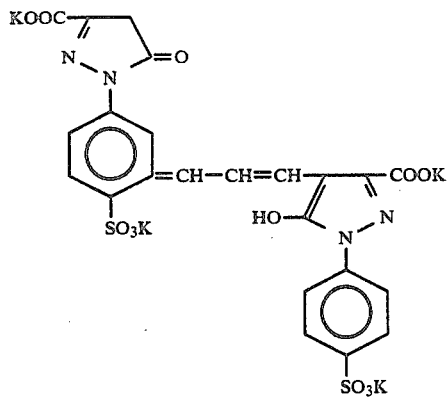
D-3
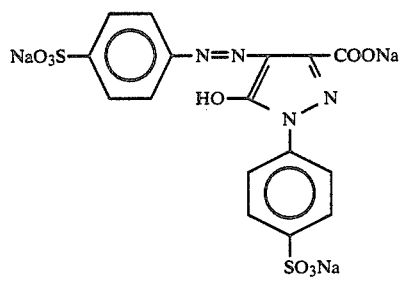
D-4
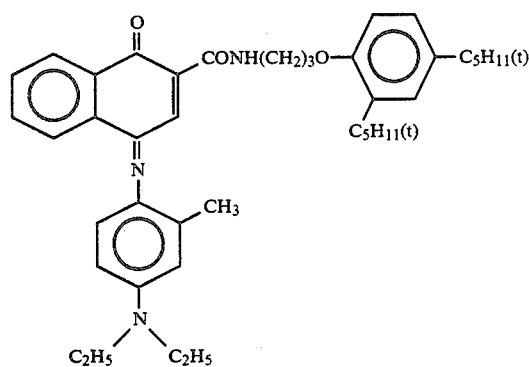
H-1
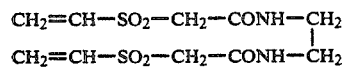
W-1
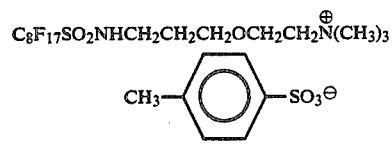
W-2
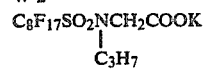
W-3
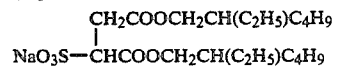
W-4

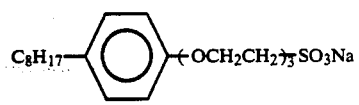
P-1
M-1
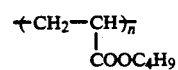
F-1
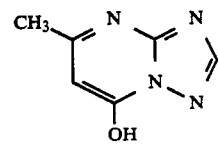
F-2
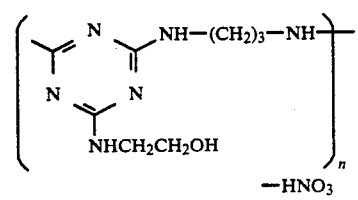
F-3
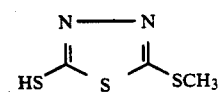
F-4
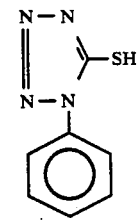
F-5
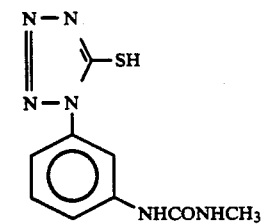
F-6
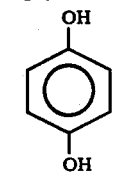
F-7

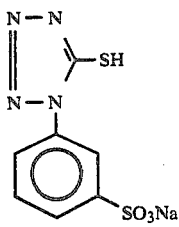

F-8

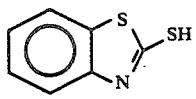

Samples 302 to 304 were prepared in the same manner as for Sample 301, except for replacing the coupler used in the 15th, 16th, and 17th layers (Coupler (9)) with the equimolar amount of Coupler (10), Coupler (13), and Coupler (7), respectively.

Each of Samples 301 to 304 was imagewise exposed to blue light and subjected to color development processing according to the following procedure. As a result, a satisfactory yellow dye image was obtained on each sample.

Development Processing Procedure:

| Step | Time (min) | Temp. (°C.) | Rate of Replenishment* (l/m2) | Volume of Tank (l) |
|---|---|---|---|---|
| Black-and-white development | 6 | 38 | 2.2 | 12 |
| First washing | 2 | 38 | 7.5 | 4 |
| Reversing | 2 | 38 | 1.1 | 4 |
| Color development | 6 | 38 | 2.2 | 12 |
| Compensation | 2 | 38 | 1.1 | 4 |
| Bleach | 6 | 38 | 0.22 | 12 |
| Fixing | 4 | 38 | 1.1 | 8 |
| Second washing | 4 | 38 | 7.5 | 8 |
| Stabilization | 1 | 25 | 1.1 | 2 |

The processing solutions used had the following formulations.

| Black-and-White Developing Solution Formulation: | Running Solution (g) | Replenisher (g) |
|---|---|---|
| Pentasodium nitrilo-N,N,N-trimethylenephosphonate | 2.0 | 2.0 |
| Sodium sulfite | 30 | 30 |
| Potassium hydroquinone monosulfonate | 20 | 20 |
| Potassium carbonate | 33 | 33 |
| 1-Phenyl-4-methyl-4-hydroxymethyl-3-pyrazolidone | 2.0 | 2.0 |
| Potassium bromide | 2.5 | 1.4 |
| Potassium thiocyanate | 1.2 | 1.2 |
| Potassium iodide | 2.0 mg | — |
| Water to make | 1.0 l | 1.0 l |
| pH (adjusted with hydrochloric acid or potassium hydroxide) | 9.60 | 9.60 |
| Reversing Bath Formulation: | | |
| The running solution and replenisher had the same composition. | | |
| Pentasodium nitrilo-N,N,N-trimethylenephosphonate | 3.0 g | |
| Stannous chloride dihydrate | 1.0 g | |
| p-Amylphenol | 0.1 g | |
| Sodium hydroxide | 8 g | |
| Glacial acetic acid | 15 ml | |
| Water to make | 1000 ml | |

| | Running Solution (g) | Replenisher (g) |
|---|---|---|
| pH (adjusted with hydrochloric acid or sodium hydroxide) | 6.00 | |
| Color Developing Solution Formulation: | | |
| Pentasodium nitrilo-N,N,N-trimethylenephosphonate | 2.0 | 2.0 |
| Sodium sulfite | 7.0 | 7.0 |
| sodium teritary phosphate 12 hydrate | 36 | 36 |
| Potassium bromide | 1.0 | — |
| Potassium iodide | 90 mg | — |
| Sodium hydroxide | 3.0 | 3.0 |
| Citrazinic acid | 1.5 | 1.5 |
| N-Ethyl-(β-methanesulfonamido-ethyl)-3-methyl-4-aminoaniline sulfate | 11 | 11 |
| Polyoxyethylene p-monononyl phenyl ether (average degree of polymerization: 10) | 0.5 ml | 0.5 ml |
| Water to make | 1.0 l | 1.0 l |
| pH (not adjusted) | | |
| Sorbitan Ester*: | | |

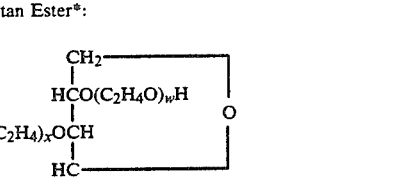

$(w + x + y + z = 20)$

While the invention has been described in detail and with reference to specific examples thereof, it will be apparent to one skilled in the art that various changes and modifications can be made therein without departing from the spirit and scope thereof.

What is claimed is:

1. A silver halide color light-sensitive material containing a coupler represented by formula (I):

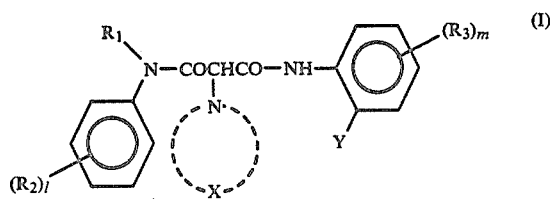

wherein $R_1$ is a substituted or unsubstituted alkyl group; $R_2$ and $R_3$, same or different, each represent a group capable of substituting a benzene ring; Y is a halogen atom, an alkoxy group, an alkoxycarbonyl group, a substituted or unsubstituted alkyl group, an alkylthio group, an aryloxy group, an alkylsulfonyl group, an arylthio group, or a carbamoyl group; X is an organic residue necessary to form a substituted or unsubstituted 5- or 6-membered nitrogen-containing heterocyclic ring together with the nitrogen atom; represents 0 or an integer of from 1 to 5; and m represents 0 or an integer of from 1 to 4.

2. The silver halide color light-sensitive material recited in claim 1, wherein:
   $R_1$ is a straight chain, branched chain or cyclic, saturated or unsaturated, substituted or unsubstituted alkyl group having from 1 to 20 carbon atoms (exclusive of any substituents);
   $R_2$ and $R_3$, same or different, are a halogen atom, an alkoxycarbonyl group having from 2 to 30 carbon atoms, an acylamino group having from 2 to 30 carbon atoms, a sulfonamido group having from 1 to 30 carbon atoms, a carbamoyl group having from 2 to 30 carbon atoms, a sulfamoyl group having from 1 to 30 carbon atoms, an alkoxy group having from 1 to 30 carbon atoms, a substituted or unsubstituted, saturated or unsaturated, alkyl group having from 1 to 20 carbon atoms (exclusive of any substituents), an N-acylsulfamoyl group having from 2 to 30 carbon atoms, a sulfonyl group having from 1 to 30 carbon atoms, an alkoxycarbonylamino group having from 1 to 30 carbon atoms, a cyano group, a nitro group, or a carboxyl group, with the proviso that when l and m are 2 or more then the plural $R_2$ and $R_3$ groups, respectively, may be the same or different;
   Y is a halogen atom, an alkoxy group having from 1 to 30 carbon atoms, an alkoxycarbonyl group having from 1 to 30 carbon atoms, a substituted or unsubstituted, saturated or unsaturated, alkyl group having from 1 to 20 carbon atoms (exclusive of any substituents), an alkylthio group having from 1 to 30 carbon atoms, an aryloxy group having from 6 to 10 carbon atoms, an alkylsulfonyl group having from 1 to 30 carbon atoms, an arylthio group having from 6 to 10 carbon atoms, or a carbamoyl group having from 2 to 30 carbon atoms; and
   the 5- or 6-membered heterocyclic group formed by X and the N atom is a monocyclic or condensed, substituted or unsubstituted heterocyclic group having 2 to 30 carbon atoms (inclusive of any substituent).

3. The silver halide color light sensitive material recited in claim 1, wherein:
   $R_1$ is a straight chain, branched chain or cyclic, saturated or unsaturated, substituted or unsubstituted alkyl group having from 1 to 10 carbon atoms (exclusive of any substituents);
   $R_2$ and $R_3$, same or different, are a halogen atom, an alkoxy-carbonyl group having from 2 to 20 carbon atoms, an acylamino group having from 2 to 20 carbon atoms, a sulfonamido group having from 1 to 20 carbon atoms, a carbamoyl group having from 2 to 20 carbon atoms, a sulfamoyl group having from 1 to 20 carbon atoms, an alkoxy group having from 1 to 20 carbon atoms, a substituted or unsubstituted, saturated or unsaturated, alkyl group having 1 to 10 carbon atoms (exclusive of any substituents), an N-acylsulfamoyl group having from 2 to 20 carbon atoms, a sulfonyl group having from 1 to 20 carbon atoms, an alkoxycarbonylamino group having from 1 to 20 carbon atoms, a cyano group, a nitro group, or a carboxyl group, with the proviso that when l or m represents 2 or more then the plural $R_2$ and $R_3$ groups, respectively, may be the same or different;
   Y is a halogen atom, an alkoxy group having from 1 to 20 carbon atoms, an alkoxycarbonyl group having from 1 to 20 carbon atoms, a substituted or unsubstituted, saturated or unsaturated, alkyl group having 1 to 10 carbon atoms (exclusive of any substituents), an alkylthio group having from 1 to 20 carbon atoms, an aryloxy group having 6 carbon atoms, an alkylsulfonyl group having from 1 to 20 carbon atoms, an arylthio group having 6 carbon atoms, or a carbamoyl group having from 2 to 20 carbon atoms; and
   the 5- or 6-membered heterocyclic group formed by X and the N atom is a monocyclic or condensed, substituted or unsubstituted heterocyclic group having 3 to 20 carbon atoms (inclusive of any substituents).

4. The silver halide color light-sensitive material recited in claim 3, wherein
   $R_1$ is substituted by a halogen atom, an alkoxy group having from 1 to 20 carbon atoms, a cyano group, a sulfonyl group having from 1 to 20 carbon atoms, an alkoxycarbonyl group having from 1 to 20 carbon atoms, an aryl group having from 6 to 10 carbon atoms, an aryloxy group having from 6 to 10 carbon atoms, an alkylthio group having from 1 to 20 carbon atoms, or a carboxyl group.

5. The silver halide color light-sensitive material recited in claim 3, wherein:
   the 5- or 6-membered heterocyclic group formed by X and the N atom is selected from the group consisting of:
   succinimido, maleinimido, phthalimido, diglycolimido, pyrrolino, pyrazolyl, imidazolyl, 1,2,4-triazol-2-yl, 1,2,4-triazol-4-yl, 1-tetrazolyl, indolyl, benzopyrazolyl, benzimidazolyl, benzotriazolyl, imidazolidine-2,4-dion-3-yl, imidazolidine-2,4-dion-1-yl, oxazolidine-2,4-dion-3-yl, thiazolidine-2,4-dion-3-yl, imidazolin-2-on-1-yl, oxazolin-2-on-3-yl, thiazolin-2-on-3-yl, benzoxazolin-2-on-3-yl, 1,2,4-triazolidine-3,5-dion-2-pyridon-1-yl, morpholine-3,5-dion-4-yl, 1,2,3-triazol-1-yl, and 2-imidazolin-5-one.

6. The silver halide color light-sensitive material recited in claim 5, wherein the 5- or 6-membered heterocyclic group formed by X and the adjacent N atom is substituted by a substituent selected from:
   a halogen atom, a hydroxyl group, a nitro group, a cyano group, a carboxyl group or a salt thereof, a sulfo group or a salt thereof, a sulfonate group, a sufinate group, an alkyl group, an alkoxy group, an acyl group, an alkoxycarbonyl group, a carbamoyl group, a sulfonyl group, a sulfamoyl group, a carbonamido group, a sulfonamido group, an amino group, an aryloxycarbonyl group, and an alkylthio group.

7. The silver halide color light-sensitive material recited in claim 1, wherein:

R₁ is a straight chain, branched chain or cyclic, saturated or unsaturated, alkyl group having from 1 to 3 carbon atoms (exclusive of any substituents);

R₂ and R₃, same or different, are a halogen atom, a substituted or unsubstituted, saturated or unsaturated, alkyl group having 1 to 3 carbon atoms (exclusive of any substituents), methoxycarbonyl, dodecyloxycarbonyl, hexadecyloxycarbonyl, acetamido, tetradecaneamido, 2-(2,4-di-t-amylphenoxy)butaneamido, benzamido, methanesulfonamido, dodecanesulfonamido, hexadecanesulfonamido, benzenesulfonamido, N-butylcarbamoyl, N,N-diethylcarbamoyl, N-butylsulfamoyl, N-dodecylsulfamoyl, N-hexadecylsulfamoyl, N-3-(2,4-di-t-amylphenoxy)butylsulfamoyl, methoxy, dodecyloxy, N-propanoylsulfamoyl, N-tetradecanoylsulfamoyl, methanesulfonyl, octanesulfonyl, dodecanesulfonyl, methoxycarbonylamino, tetradecyloxycarbonylamino, a cyano group, a nitro group, or a carboxyl group with the proviso that when l or m are 2 or more then the plural R₂ and R₃ groups, respectively, may be the same or different;

Y is a halogen atom, a substituted or unsubstituted, saturated or unsaturated, alkyl group having 1 to 3 carbon atoms (exclusive of any substituents), methoxy, ethoxy, tetradecyloxy, methoxycarbonyl, butoxycarbonyl, methylthio, butylthio, methanesulfonyl, dodecylsulfonyl, or N-dodecylcarbamoyl; and the 5- or 6-membered heterocyclic group formed by X and the adjacent N atom is a monocyclic or condensed, substituted or unsubstituted heterocyclic group selected from the group consisting of:

1-pyrazolyl, imidazolyl, 1,2,3-triazol-1-yl, benzotriazolyl, 1,2,4-triazol-1-yl, oxazolidine-2,4-dion-3-yl, 1,2,4-triazolidine-3,5-dion-4-yl, and imidazolidine-2,4-dion-3-yl groups, each of which heterocyclic groups may be substituted by one or more of the following:

a halogen atom, a hydroxyl group, a nitro group, a cyano group, a carboxyl group or salt thereof, a sulfo group or a salt thereof, a sulfinate group, a sulfonate group, methyl, ethyl, n-decyl, t-butyl, trifluoromethyl, carboxymethyl, methoxy, ethoxy, methoxyethoxy, acetyl, benzoyl, methoxycarbonyl, isoamyloxycarbonylmethoxycarbonyl, ethoxycarbonyl, i-propoxycarbonyl, n-dodecyloxycarbonyl, N,N-dimethylcarbamoyl, N-phenylcarbamoyl, N-methoxyethylcarbamoyl, N-tetradecylcarbamoyl, methanesulfonyl, benzenesulfonyl, 4-hydroxybenzenesulfonyl, N-methylsulfamoyl, N-phenylsulfamoyl, N-dodecylsulfamoyl, acetamido, benzamido, trifluoroacetamido, pentafluorobenzamido, methanesulfonamido, p-toluenesulfonamido, amino, N,N-dimethylamino, N,N-diethylamino, pyrrolidino, piperidino, phenoxycarbonyl, hexylthio, and octylthio.

8. The silver halide color light-sensitive material recited in claim 7, wherein

R₁ is substituted by one or more of the following:
a halogen atom, an alkoxy group having from 1 to 10 carbon atoms, a cyano group, a sulfonyl group having from 1 to 10 carbon atoms, an alkoxycarbonyl group having from 1 to 10 carbon atoms, an aryl group having from 6 to 10 carbon atoms, an aryloxy group having from 6 to 10 carbon atoms, an alkylthio group having from 1 to 10 carbon atoms, and a carboxyl group.

9. The silver halide color light-sensitive material recited in claim 1, wherein the coupler represented by Formula (I) is also represented by Formula (III):

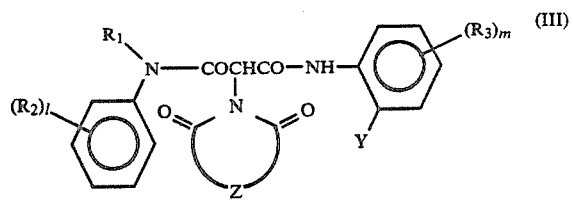

wherein
R₁, R₂, R₃, Y, l, and m are as defined in claim 1, and Z forms a heterocyclic group and is

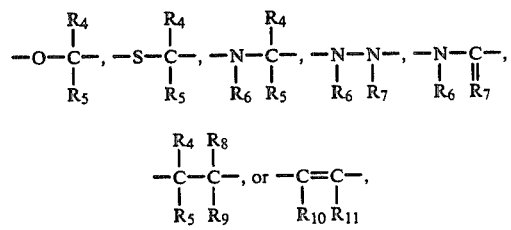

wherein
R₄, R₅, R₈, and R₉, same or different, each is a hydrogen atom, an alkyl group, an aryl group, an alkoxy group, an aryloxy group, an alkylthio group, arylthio group, an alkylsulfonyl group, an arylsulfonyl group, or an amino group; R₆ and R₇, same or different, each is a hydrogen atom, an alkyl group, an aryl group, an alkylsulfonyl group, an arylsulfonyl group, or an alkoxycarbonyl group; R₄ and R₅, R₅ and R₆, R₆ and R₇, or R₄ and R₈ each may be taken together to form a ring; and R₁₀ and R₁₁, same or different, each represent a hydrogen atom, an alkyl group, or an aryl group, or they may be taken together to form a benzene ring.

10. The silver halide color light-sensitive material recited in claim 9, wherein the heterocyclic group formed by Z contains from 2 to 30 carbon atoms.

11. The silver halide color light-sensitive material recited in claim 9, wherein the heterocyclic group formed by Z is one of the following moieties:

succinimide, maleinimido, phthalimido, 1-methylimidazolidine-2,4-dion-3-yl, 1-benzylimidazolidine-2,4-dion-3-yl, 5,5-dimethyloxazolidine-2,4-dion-3-yl, 5-methyl-5-propyloxazolidine-2,4-dion-3-yl, 5,5-dimethylthiazolidine-2,4-dion-3-yl, 5,5-dimethylimidazolidine-2,4-dion-3-yl, 3-methylimidazolidinetrion-1-yl, 1,2,4-triazolidine-3,5-dion-4-yl, 1-methyl-2-phenyl-1,2,4-triazolidine-3,5-dion-4-yl, 1-benzyl-2-phenyl-1,2,4-triazolidine-3,5-dion-4-yl, 5-hexyloxy-1-methylimidazolidine-2,4-dion-3-yl, 1-benzyl-5-ethoxyimidazolidine-2,4-dion-3-yl, or 1-benzyl-5-dodecyloxyimidazolidine-2,4-dion-3-yl.

12. The silver halide color light-sensitive material recited in claim 1, wherein Y is a halogen atom, an alkoxy group, or an alkoxycarbonyl group.

13. The silver halide color light-sensitive material recited in claim 1, wherein the coupler represented by Formula (I) is a nondiffusible coupler.

14. The silver halide color light-sensitive material recited in claim 1, wherein the 5- or 6-membered heterocyclic group formed by X and the N atom is selected from the group consisting of:
succinimido, maleinimido, phthalimido, diglycolimido, pyrrolino, pyrazolyl, imidazolyl, 1,2,4-triazol-2-yl, 1,2,4-triazol-4-yl, 1-tetrazolyl, indolyl, benzopyrazolyl, benzimidazolyl, benzotriazolyl, imidazolidine-2,4-dion-3-yl, imidazolidine-2,4-dion-1-yl, oxazolin-2-on-3-yl, thiazolin-2-on-3-yl, benzoxazolin-2-on-3-yl, 1,2,4-triazolidine-3,5-dion-4-yl, and 2-imidazolin-5-one.

15. The silver halide color light-sensitive material recited in claim 14, wherein the 5- or 6-membered heterocyclic group formed by X and the adjacent N atom is substituted by a substituent selected from:
a halogen atom, a hydroxyl group, a nitro group, a cyano group, a carboxyl group or a salt thereof, a sulfo group or a salt thereof, a sulfonate group, a sulfinate group, an alkyl group, an alkoxy group, an acyl group, an alkoxycarbonyl group, a carbamoyl group, a sulfonyl group, a sulfamoyl group, a carbonamido gorup, a sulfonamido group, an amino group, an aryloxycarbonyl group, and an alkylthio group.

16. The silver halide color light-sensitive material recited in claim 1, wherein the coupler represented by formula (I) is a DIR coupler represented by formula (II):

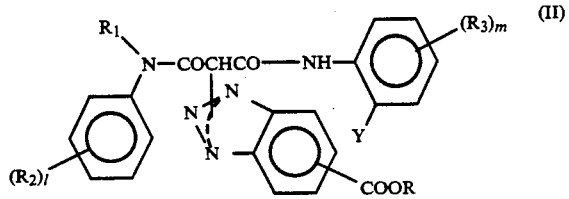

wherein $R_1$, $R_2$, $R_3$, Y, l, and m are as defined in claim 1; and R represents a substituted or unsubstituted alkyl group having from 1 to 4 carbon atoms (exclusive of any substituent).

17. The silver halide color light-sensitive material recited in claim 16, wherein R is a straight chain or branched chain, substituted or unsubstituted, saturated or unsaturated, alkyl group having 1 to 4 carbon atoms (exclusive of any substituents).

18. The silver halide color light-sensitive material recited in claim 17, wherein R is substituted by one or more or the following:
an alkoxycarbonyl group having from 2 to 6 carbon atoms, a carbamoyl group having from 1 to 9 carbon atoms, a halogen atom, a nitro group, a cyano group, an alkoxy group having from 1 to 4 carbon atoms, a sulfamoyl group having up to 6 carbon atoms, an aryloxy group having from 6 to 10 carbon atoms, an acyl group having from 2 to 7 carbon atoms, a sulfonyl group having from 1 to 6 carbon atoms, a 3- to 6-membered heterocyclic group having from 1 to 5 carbon atoms and a hetero atom selected from nitrogen, oxygen and sulfur atoms, and phosphoryl group having from 2 to 5 carbon atoms.

19. The silver halide color light-sensitive material recited in claim 17, wherein R is substituted by one or more of the following:
an alkoxycarbonyl group having from 2 to 67 carbon atoms, and a carbamoyl group having from 1 to 9 carbon atoms.

20. The silver halide color light-sensitive material recited in claim 17, wherein R is substituted by one or more of the following:
methoxycarbonyl, propoxycarbonyl, butoxycarbonyl, isobutoxycarbonyl, isopropoxycarbonyl, pentyloxycarbonyl, isopentyloxycarbonyl, 2-methoxyethoxycarbonyl, N,N-diethylcarbamoyl, N-methyl-N-ethylcarbamoyl, N-hexylcarbamoyl, pyrrolidinocarbonyl, piperidinocarbonyl, a halogen atom, a nitro group, a cyano group, methoxy, ethoxy, methoxyethoxy, N,N-diethylsulfamoyl, N-methyl-N-ethylsulfamoyl, 4-chlorophenoxy, acetyl, benzoyl, methanesulfanoyl, butanesulfonyl, 2-pyridyl, 3-pyridyl, and O,O-diethylphosphoryl.

* * * * *